United States Patent
Duggal et al.

(10) Patent No.: US 8,303,631 B2
(45) Date of Patent: Nov. 6, 2012

(54) SYSTEMS AND METHODS FOR POSTERIOR DYNAMIC STABILIZATION

(75) Inventors: Neil Duggal, London (CA); T. Wade Fallin, Hyde Park, UT (US); Dylan M. Hushka, Chandler, AZ (US); Joshua A. Butters, Chandler, AZ (US)

(73) Assignees: Neil Duggal, London Ontario (CA); MedicineLodge Inc., Logan, UT (US)

( * ) Notice: Subject to any disclaimer, the term of this patent is extended or adjusted under 35 U.S.C. 154(b) by 463 days.

(21) Appl. No.: 12/486,563

(22) Filed: Jun. 17, 2009

(65) Prior Publication Data

US 2009/0318968 A1 Dec. 24, 2009

Related U.S. Application Data

(60) Provisional application No. 61/074,534, filed on Jun. 20, 2008.

(51) Int. Cl.
  *A61B 17/70* (2006.01)
(52) U.S. Cl. ......................................................... 606/250
(58) Field of Classification Search ........... 606/246–267
  See application file for complete search history.

(56) References Cited

U.S. PATENT DOCUMENTS

| | | | |
|---|---|---|---|
| 6,585,769 B1 | 7/2003 | Muhanna | |
| 7,115,142 B2 | 10/2006 | Muhanna | |
| 7,867,263 B2* | 1/2011 | Lowry et al. | 606/281 |
| 8,012,181 B2* | 9/2011 | Winslow et al. | 606/257 |
| 2004/0049190 A1 | 3/2004 | Biedermann | |
| 2005/0203511 A1 | 9/2005 | Wilson-MacDonald | |
| 2005/0209694 A1 | 9/2005 | Loeb | |
| 2006/0084982 A1* | 4/2006 | Kim | 606/61 |
| 2006/0084991 A1 | 4/2006 | Borgstrom | |
| 2006/0241769 A1 | 10/2006 | Gordon | |
| 2006/0247637 A1 | 11/2006 | Colleran | |
| 2006/0264948 A1 | 11/2006 | Williams | |
| 2006/0287723 A1 | 12/2006 | Muhanna | |
| 2007/0055373 A1 | 3/2007 | Hudgins | |
| 2007/0073289 A1* | 3/2007 | Kwak et al. | 606/61 |
| 2007/0073293 A1 | 3/2007 | Martz | |
| 2007/0233089 A1 | 10/2007 | DiPoto | |
| 2008/0114357 A1 | 5/2008 | Allard | |
| 2008/0132954 A1 | 6/2008 | Sekhon | |
| 2008/0281358 A1* | 11/2008 | Abdou | 606/246 |
| 2009/0093819 A1 | 4/2009 | Joshi | |

FOREIGN PATENT DOCUMENTS

WO WO2006116853 11/2006

* cited by examiner

*Primary Examiner* — Alvin Stewart
*Assistant Examiner* — James Palmer
(74) *Attorney, Agent, or Firm* — Peter K. Johnson; James Larson; Barbara Daniels

(57) ABSTRACT

A system for providing dynamic stabilization and balance control at a vertebral motion segment has first and second bridge elements and at least one bias element. The bridge elements anchor to adjacent vertebrae with polyaxially adjustable anchoring members, and the bias elements attach to each bridge element to span between them. Each bias element has two fixation portions and a bias body extending between the fixation portions. Each bias element may comprise an elastically deformable material to provide dynamic stabilization with motion, or may comprise rigid material to provide rigid stabilization, and both bias element types may be included in one system. The bias elements are attachable to the bridge elements at discrete attachment locations, or at non-discrete attachment locations. Alternate embodiments may include three or more bridge elements on adjacent vertebrae, and multiple bias elements. A tensioning tool may provide adjustable tension to an elastically deformable bias element.

67 Claims, 15 Drawing Sheets

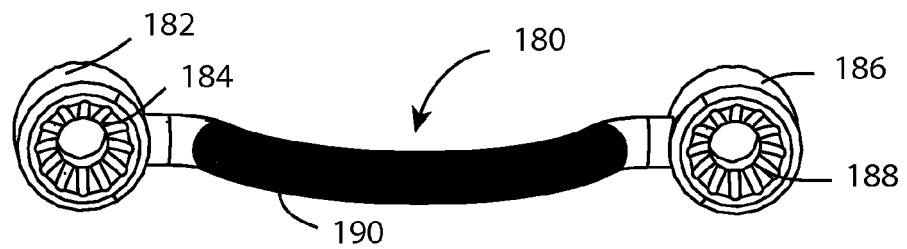
Fig. 15A
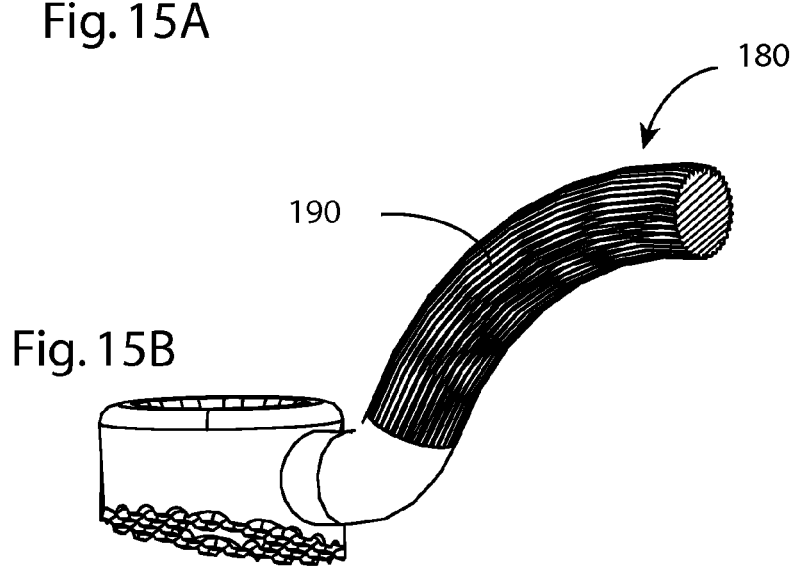
Fig. 15B
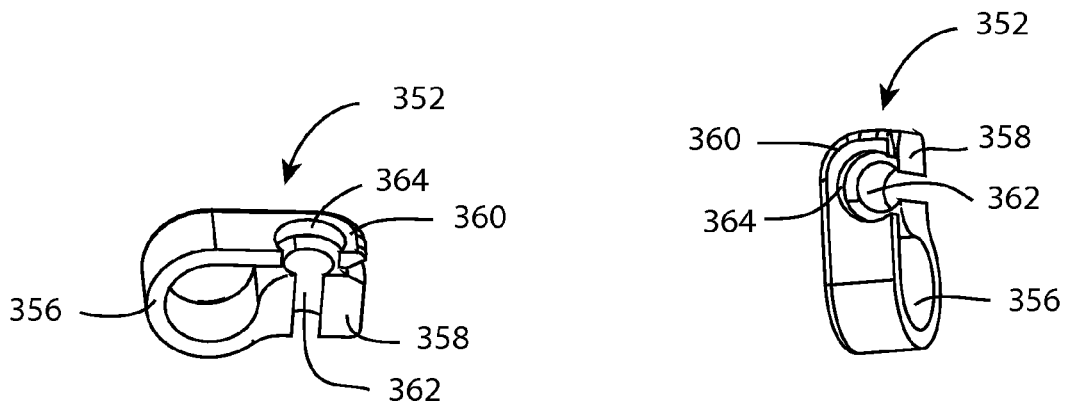
Fig. 15C
Fig. 15D

SYSTEMS AND METHODS FOR POSTERIOR DYNAMIC STABILIZATION

CROSS-REFERENCE TO RELATED APPLICATIONS

This application claims the benefit of:

U.S. Provisional Patent Application No. 61/074,534, filed Jun. 20, 2008, which is entitled POSTERIOR DYNAMIC STABILIZATION SYSTEM.

The above-identified document is incorporated herein by reference.

BACKGROUND OF THE INVENTION

1. The Field of the Invention

The invention relates to orthopaedics, and more particularly, to systems and methods for treatment for the cervical or thoracolumbar spine that embody both principles of providing motion restoration as well as balance control.

2. The Relevant Technology

Cervical spondylosis is an almost universal concomitant of human aging. More than half of middle-age populations have radiographic or pathologic evidence of cervical spondylosis. Spondylosis with resulting cord compression is the pathogenic factor in 55% of cervical myelopathy cases. The exact pathophysiology of cervical spondylotic myelopathy (CSM) remains unclear. Some proposed mechanisms include direct mechanical compression, microtrauma and ischemia to the cervical spinal cord.

A variety of factors have been implicated as predictors of clinical outcome following surgery. These include age, duration of symptoms prior to surgery, severity of myelopathy before surgery, multiplicity of involvement, anteroposterior canal diameter, transverse area of the spinal cord and high-signal intensity area on T2-weighted imaging.

Surgery is reserved for patients with a progressive history of worsening signs or symptoms, severe spinal cord compression found on imaging studies and failure to respond to nonoperative treatment. Operative treatment is directed at relieving the spinal cord compression by expanding the spinal canal diameter. Surgical options include anterior discectomy and fusion (ACDF), corpectomy, laminectomy with or without fusion, and laminoplasty. The choice of an anterior or posterior approach to decompression is influenced by several factors: the degree of disc herniation, osteophyte formation, ligamentous hypertrophy, facet degeneration, number of levels involved, spinal alignment and mobility must all be taken into consideration. A relative indication for an anterior approach, including corpectomy or cervical discectomy and fusion, is the pre-operative presence of cervical kyphosis or straightening of cervical spine. In such circumstances, an anterior single or multilevel approach restores the alignment of the anterior and middle columns, avoiding post-laminectomy progression of kyphosis with worsening deficit. However, multi-level anterior procedures may be associated with significant risks and potential complications. In the setting of myelopathy secondary to multilevel posterior disease, particularly in the elderly, a posterior approach may be more appropriate.

For patients with a neutral to lordotic cervical alignment, laminoplasty has been advocated as an alternative to laminectomy and fusion or multi-level corpectomy. Laminoplasty has the theoretical advantage of preserving spinal motion. Unfortunately, laminoplasty is not indicated in the setting of pre-operative cervical straightening or kyphosis. In the setting of straightening, pre-operative kyphotic deformity or degenerative spondylosis in the subaxial spine, laminectomy alone has been implicated in the development iatrogenic post-laminectomy kyphosis. Removal of the interspinous ligaments, ligamentum flavum along with devascularization of the paravertebral muscles has been implicated in the loss of the "posterior tension band" in decompression cases. Unfortunately, multi-level decompression and fusion can be associated with significant loss of range of motion for the subaxial cervical spine. In addition, multilevel fusion can be associated with significant risks for adjacent segment degeneration.

Laminectomy remains a mainstay of surgical decompression for multi-level CSM. However, drawbacks include the risks of post-laminectomy kyphosis, instability, accelerated spondylotic changes, and late neurological deficit. Post-laminectomy kyphosis is twice as likely to develop if there is preoperative loss of the normal cervical lordosis. Laminectomy with concomitant posterolateral fusion has been advocated as a means of attaining neural decompression while avoiding iatrogenic kyphosis. Fusion has, however, the disadvantage of converting a functionally mobile, mechanically stable spinal unit into a fixed, nonfunctional one. Analysis of strain distribution in intervertebral discs following fusion has shown an increase in longitudinal strain, most commonly at levels immediately adjacent to the fused segments. The resultant increase in stress on discs adjacent to the fused levels is thought to lead to accelerated disc degeneration and/or mechanical instability at adjacent levels. Radiographic changes of spondylosis and instability at levels above and below cervical fusions have been described by several authors. No motion sparing surgical solution currently exists for these patients. Therefore, a need exists for technology that allows reconstitution of the posterior tension band following decompression with laminectomy.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 15A provides a posterior perspective view of a bridge element of the dynamic stabilization system of FIG. 14;

FIG. 15B provides a perspective view of a portion of the bridge element of FIG. 15A;

FIG. 15C a perspective view of a clamp of the dynamic stabilization system of FIG. 14; and FIG. 15D provides a perspective view of the clamp of FIG. 15C.

DETAILED DESCRIPTION OF THE PREFERRED EMBODIMENTS

The present invention relates to systems and methods for providing dynamic stabilization between spinal segments. Those of skill in the art will recognize that the following description is merely illustrative of the principles of the invention, which may be applied in various ways to provide many different alternative embodiments. This description is made for the purpose of illustrating the general principles of this invention and is not meant to limit the inventive concepts in the appended claims.

Disclosed herein is a novel technology that allows reconstitution of the posterior tension band following decompression with laminectomy. The system allows semi-constrained motion between the spinal segments, preserving the normal mobility of the spine, while providing a restoring force that prevents post-operative kyphosis as well as allows correction of pre-existing deformity in the sagittal and/or coronal planes. Thus the system provides motion restoration with the addition of balance control. In an implantation procedure, lateral mass screws may be placed with a modified Magerl technique using anatomic landmarks. Laminectomy may be performed following placement of the screws and the decompression is achieved. Alternately, screws may be placed first, followed by laminectomy. Finally, the novel posterior cervical dynamic stabilization system is affixed to the cervical spine. In the lumbar or thoracic spine, the novel posterior dynamic stabilization system could be affixed via pedicle screws. The following novel embodiments could be easily adapted for the lumbar and thoracic spines.

Figure 1:
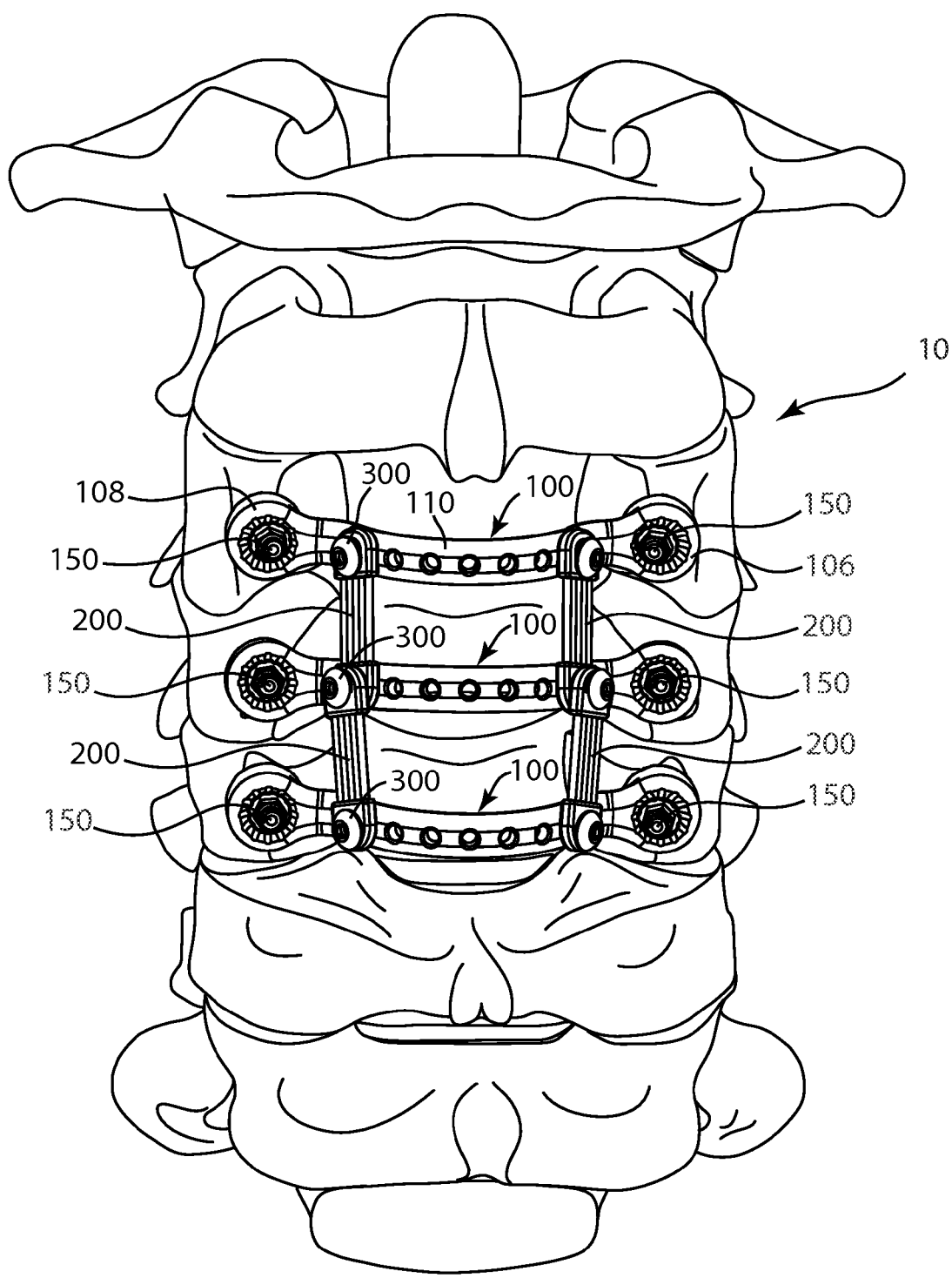
FIG. 1 provides a posterior perspective view of a dynamic stabilization system according to one embodiment of the invention, secured to a portion of a spine.

Referring to FIG. 1, one embodiment of a posterior dynamic stabilization system 10 is shown secured to a portion of a spine. In the embodiment depicted, laminectomy has been performed on the C3, C4 and C5 cervical vertebrae. The system 10 comprises at least two bridge elements 100, each of which is sized and shaped to span medial-laterally across the resected vertebra between the lateral masses. Each bridge element 100 comprises a first anchoring feature 106, a second anchoring feature 108, and a bridge body 110 extending between and connecting the anchoring features. Each bridge element 100 may be secured to a vertebra by at least one anchoring member 150. Each anchoring member 150 may comprise an anchor or screw sized and shaped to be received in an anchoring feature 106 or 108, and may interface with the anchoring feature to secure the bridge element 100 to the bone. At least one bias element 200 is attached at one end to one bridge element 100, and at another end to a second bridge element 100, via attachment mechanisms 300. Each bias element 200 may be elastically deformable to provide dynamic stabilization between the vertebrae involved. In alternative embodiments, one or more bias elements may comprise a more rigid material to provide a stiffer degree of stabilization. The system 10 depicted in FIG. 1 includes four elastically deformable bias elements, allowing semi-constrained motion between the spinal segments, preserving the normal mobility of the spine. The distribution of the bias elements may be symmetrical as seen in FIG. 1, while alternative embodiments include asymmetrically arranged bias elements.

Referring to FIGS. 2A-2D, views of bridge element 100 are seen from several perspectives. Bridge element 100 may be referred to as a laminar bridge, and is essentially a prosthetic lamina to replace the lamina that has been removed during the laminectomy for decompression. The laminar bridge preferably includes bone ingrowth contact areas that contact the bone and encourage long-term bony fixation, areas which are ideally located on the anterior faces near the bone anchor attachment location, in order to contact the posterior aspects of the lateral masses. The laminar bridge is shaped to be situated well above the thecal sac to prevent any contact with the dura. Bridge element 100 may comprise titanium, stainless steel, aluminum, cobalt chrome, Nitinol, PEEK (poly ether ether ketone), UHMWPE (ultra high molecular weight polyethylene), or other suitable sufficiently rigid biocompatible materials. In alternate embodiments, a bridge element may comprise an elastically deformable material.

The bridge elements may take many forms other than those depicted here to accomplish the same function. For example, a bridge element may comprise two or more parts instead of the monolithic version shown. The bridge may be tubular in form or include hollow portions to improve radiographic visualization if needed. In addition, the size of each bridge element can vary as needed. For example, in some cases, such as when a greater clearance of the dural sac is required on one side of the vertebra, a wider and/or longer anchoring feature may be required on such one side. Also, the length, width, thickness and/or height of the bridge body may vary as required by patient anatomy or as needed for a desired correction. A bridge element may be medial-laterally symmetrical as depicted in FIGS. 2A-2D, or asymmetrical as needed.

Each bridge element 100 comprises a first end 102 having an anchoring feature 106, and a second end 104 having an anchoring feature 108. The bridge element 100 further comprises a posterior side 112 and a generally opposite anterior side 114. A plurality of individual discretely located attachment features 118 are distributed along the bridge body 110. The attachment features, which may be threaded to engage corresponding threads on an attachment mechanism, may be distributed evenly or unevenly along the bridge body.

Figure 2A:
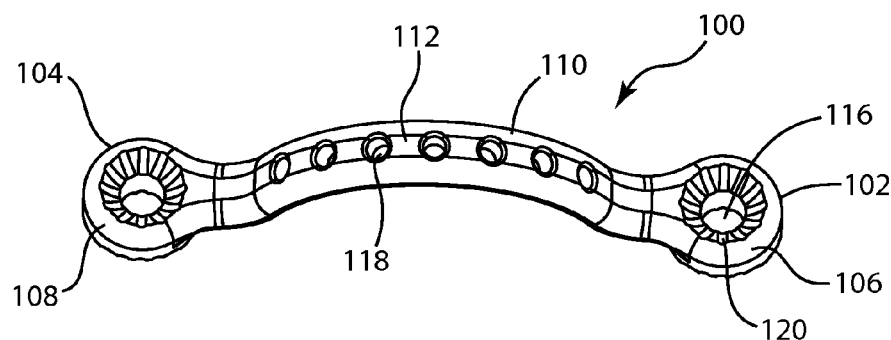
FIG. 2A provides a posterior perspective view of a bridge element of the dynamic stabilization system of FIG. 1.
Figure 2B:
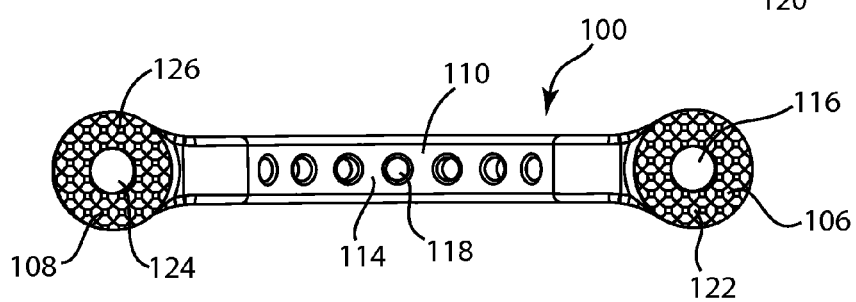
FIG. 2B provides an anterior view of the bridge element of FIG. 2A.

Referring to FIGS. 2A and 2B, anchoring feature 106 includes an aperture 116 extending from the posterior side to the anterior side of the bridge element. The aperture 116 depicted is substantially cylindrical; however in other embodiments the aperture may be tapered to accommodate polyaxial adjustability of an anchoring member received in the aperture. On the posterior side, a concave cutout 120 encircles the aperture opening. The cutout 120 allows for polyaxial adjustment of the anchoring member, and is faceted to interface with a correspondingly faceted surface of the anchoring member. In addition to or in place of faceting, the cutout may include surface features such as divots, splines, knurling, longitudinal grooves, circumferential grooves, facets, nubs, and combinations thereof, and/or include surface treatments, roughening or excoriation to promote gripping contact between the anchoring feature and the anchoring member, and to prevent unintended backout of the anchoring member.

Figure 2C:
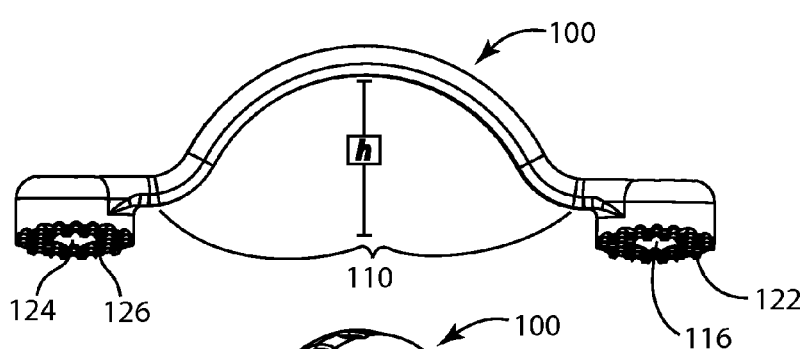
FIG. 2C provides a caudal view of the bridge element of FIG. 2A.
Figure 2D:
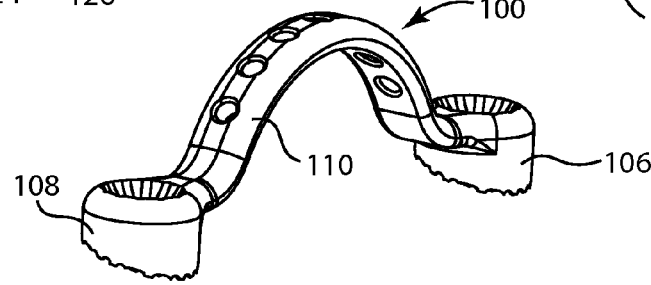
FIG. 2D provides a medial perspective view of the bridge element of FIG. 2A.

The anterior surface of the anchoring feature 106 includes a bone apposition portion 122. The bone apposition portion 122 may be knurled as depicted in FIGS. 2B and 2C, and/or may include features such as roughening, excoriation, porous structures or treatments such as porous titanium coating, plasma-sprayed titanium, hydroxylapatite coating, tricalcium phosphate coating, to promote gripping contact and to promote bony ingrowth for long-term fixation. As seen in FIGS. 2C and 2D, the anterior surface of the anchoring feature 106 may be angled relative to the posterior surface of the bridge element, to optimally correspond to the natural or resected bone surface to which it is secured during implantation. Anchoring feature 108, found at the second end 104 of the bridge element 100, includes aperture 124 and bone apposition portion 126, which correspond to those of anchoring feature 106.

As seen in FIGS. 2A-2D, bridge body 110 extends medial-laterally between anchoring feature 106 and anchoring feature 108. Bridge body 110 is curved or arched to avoid contact with the dura when implanted, and a posterior height h of the curve or arch may exceed the height of the removed natural lamina. The attachment features 118 depicted are holes, which may include threads for engagement with threaded attachment members. Other embodiments may include attachment features which are at continuous non-discrete locations along the bridge body. Other embodiments may also include attachment features configured to engage various attachment mechanisms such as clamps, threaded fasteners, locking nuts, posts, holes, press-fits, quick-release and quick-attachment connections, ¼-turn connections, t-slots, dovetail joints, living hinges, and flanges, among others. All of the attachment features 118 may be medially offset from the anchoring features 106, 108 when the bridge element 100 is properly secured to a vertebra in the manner set forth herein, that is, in a medial-lateral orientation so as to span the vertebra.

Figure 3A:
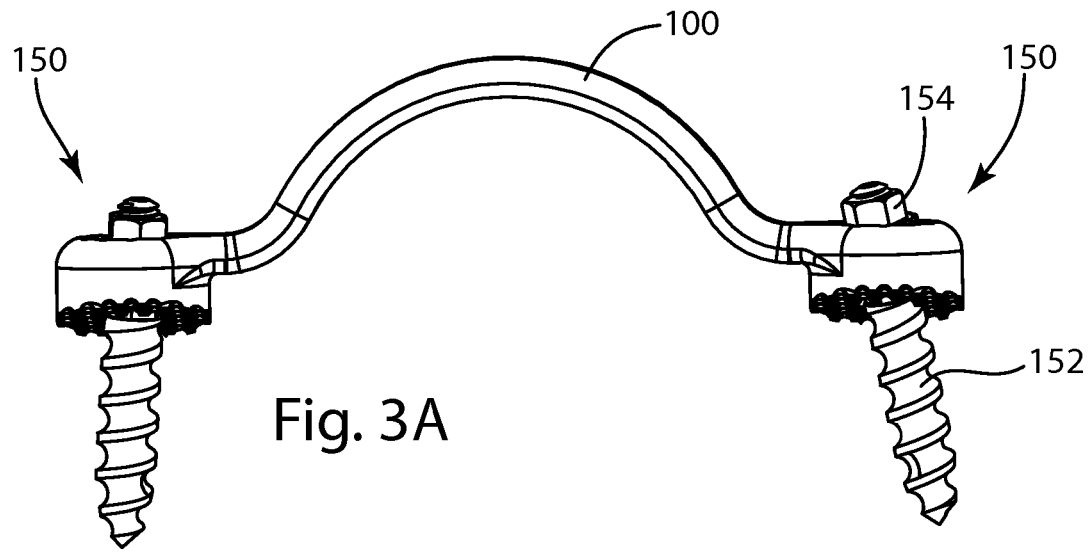
FIG. 3A provides a caudal view of a bridge element and two anchoring members of the dynamic stabilization system of FIG. 1.
Figure 3B:
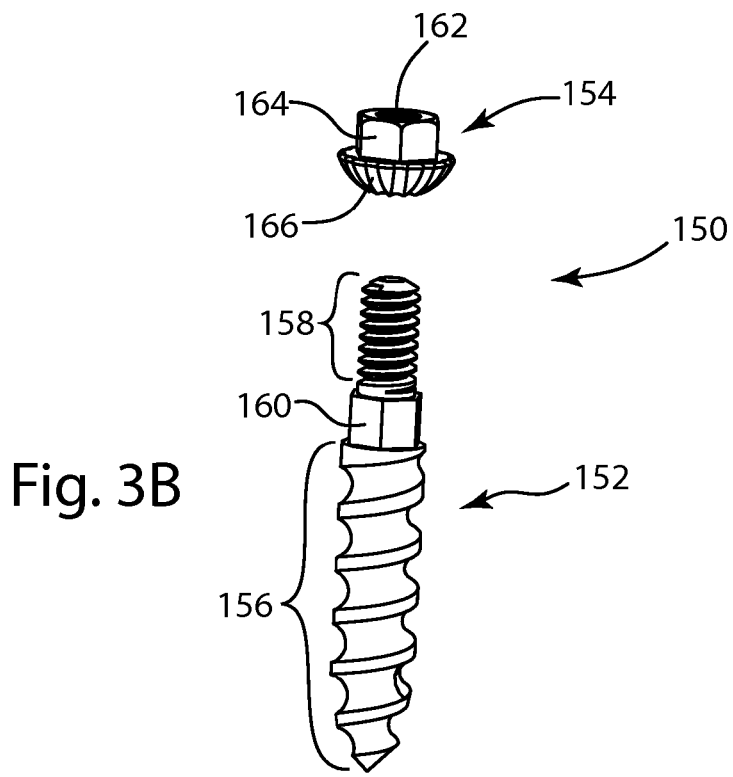
FIG. 3B provides an exploded perspective view of an anchoring member of FIG. 3A.

Referring to FIGS. 3A and 3B, a single bridge element 100 may be secured by two anchoring members 150. In the embodiment depicted, anchoring member 150 comprises bone anchor 152 and nut 154, which may be a locking nut. Bone anchor 152 comprises distal threaded portion 156, proximal threaded shank 158, and drive feature 160. In the depicted embodiment, drive feature 160 is an external hex drive and is positioned between the distal and proximal threaded portions; however in other embodiments the drive feature may be internal and/or comprise a different shape or location. For example, an alternate anchoring member may comprise a screw with a proximally located internal drive feature having a rectangular, triangular or pentagonal shape. Other suitable screw-type bone anchors may include lateral mass screws, monoaxial bone screws, polyaxial bone screws, screws with spherical heads, pedicle screws, screws with trilobular or lobular heads, tulip heads, proximal shanks, nuts, slots, serrations, or grooves, among others. Yet other anchoring members may be substituted for bone screws, such as staples, wires, cable, clamps, or hooks, among others. Anchoring members may include structures to assist in long-term fixation, including but not limited to porous titanium coating, plasma-sprayed titanium, hydroxylapatite coating, tricalcium phosphate coating, porous structures and/or rough surface treatments.

Nut 154 comprises an internal lumen 162 shaped to engage with the bone anchor 152. In the embodiment depicted, internal lumen 162 is threaded such that it may threadedly engage the proximal threaded portion 158 of the bone anchor 152. Nut 154 further comprises a drive portion 164 and an interface portion 166. The interface portion 166 is convex and comprises surface facets which correspond to the faceting of concave cutout 120 on the bridge element. Other embodiments of the interface portion 166 may comprise facets, and/or other surface features such as divots, splines, knurling, longitudinal grooves, circumferential grooves, facets, nubs, and combinations thereof, and/or include surface treatments, roughening or excoriation.

Figure 4:
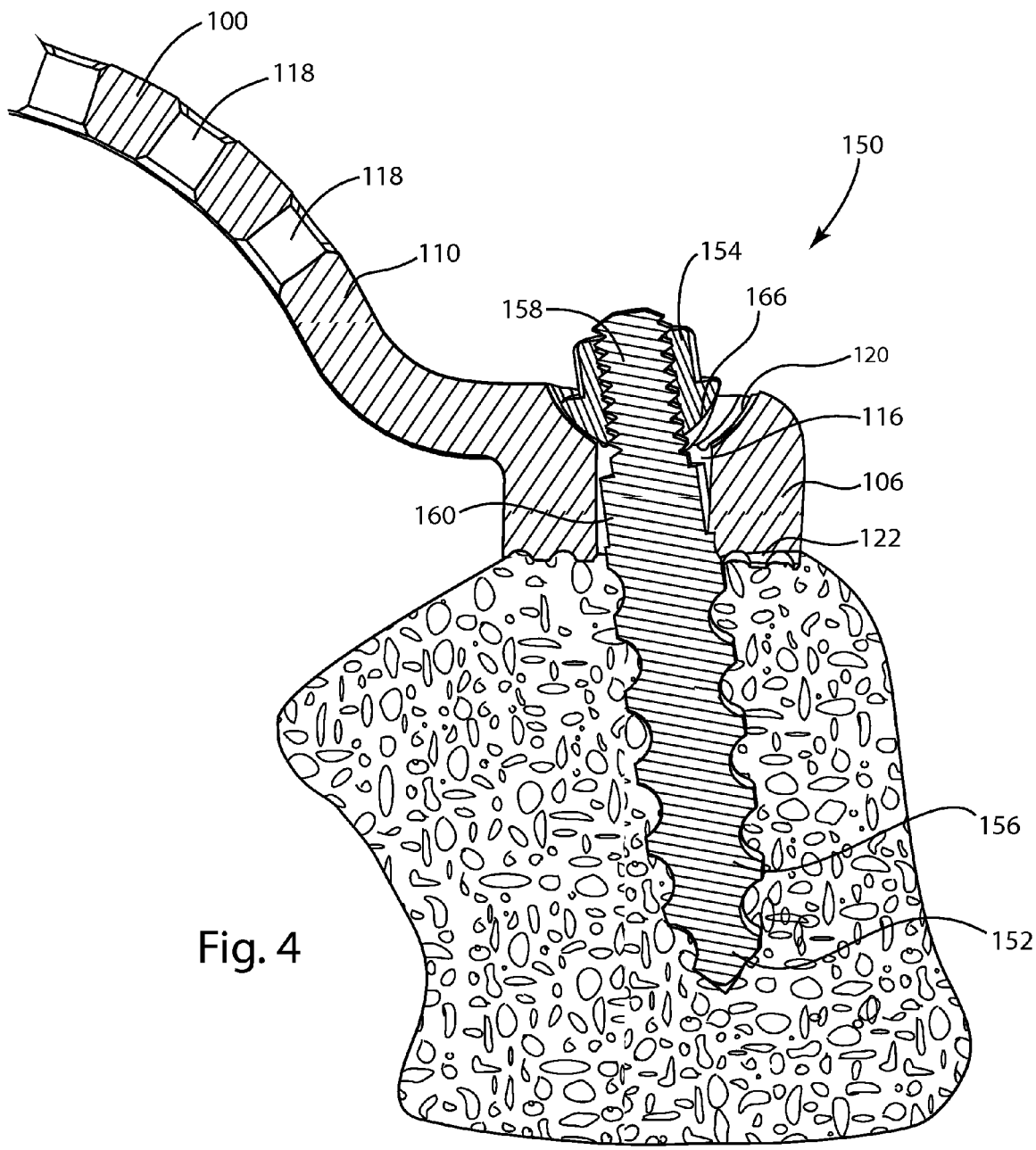
FIG. 4 provides an enlarged caudal cross-sectional view of a portion of the bridge element and one anchoring member of FIG. 3A, anchored in a vertebra.

Referring to FIG. 4, a cross-sectional view of an anchoring member 150 in engagement with a bridge member 100 is shown. Distal threaded portion 156 of bone anchor 152 is engaged in a bone, and anchoring feature 106 is placed over the bone screw such that aperture 116 surrounds drive feature 160 and bone apposition portion 122 contacts the surface of the bone. Nut 154 is threaded onto the proximal threaded shank 158 to secure bridge member 100 to the bone, and convex interface portion 166 engages with concave cutout 120. The inner diameter of concave cutout 120 is greater than the outer diameter of convex interface portion 166, to allow for polyaxial positioning of anchoring member 150. As set forth previously, aperture 116 may also be tapered at its distal, or bone-engaging, end to also allow polyaxial placement of anchoring member 150.

As seen in FIG. 1, multiple bias elements 200 are each coupled at a cephalad end to a first bridge element 100, and coupled at a caudal end to a second bridge element 100. In the embodiment shown, bias element 200 comprises a compliant, elastically deformable material which allows constrained motion between the first and second bridge elements. Such compliant, elastically deformable materials may include elastomers, silicones, urethanes, bio-absorbable materials, woven textile structures, knit textile structures, braided textile structures, molded thermoplastic polymers, ethylene-vinyl acetate, PEEK, or UHMWPE; and materials such as Nitinol, titanium, and stainless steel formed into elastically deformable structures such as springs.

The bias element is intended to replicate or partially simulate the natural posterior tension band in order to place physiologic constraints to motion and balance once these natural structures have been compromised after surgery. The preferred embodiment includes a compliant material which is suited for tension/extension, such as a silicone or elastomer. The bias element is preferably configured with two attachment ends to be secured to the laminar bridges, as well as a central portion which may be bowed posteriorly in order to encourage buckling in posterior direction during patient extension. During patient flexion, the bias element incurs tensile forces and the bias element resists those partially incurring deflection and allowing the flexion to occur. The bias element may allow all anatomic range of motions seen in the spine including flexion, extension, lateral bending and rotation. All coupled motions may be possible. The bias element may have a restoring force, preventing the development of post-laminectomy deformity. The geometry of the bias element may be configured to provide a correcting force in all planes for correction of sagittal and coronal deformities.

Referring to FIGS. 5A-5D, different configurations of elastically deformable bias elements are shown. Bias element 200 comprises a first fixation portion 202, a second fixation 204 and a bias body 206 extending between the first and second fixation portions. In the embodiment shown, the first and second fixation portions 202, 204 are each formed from a rigid material which is substantially more rigid and less compliant than the elastically deformable material. Such rigid materials may include titanium, stainless steel, aluminum, cobalt chromium, Nitinol, PEEK, and UHMWPE, among others. Each fixation portion 202, 204 comprises a joining feature 208, which in the embodiment shown, is a hole. The joining feature 208 is configured to cooperate with an attachment mechanism to join or attach the bias element to a bridge element. The bias body 206 of bias element 200 comprises five separate strands of an elastically deformable material. Other embodiments of the bias element may include more or fewer strands, and/or strands which are woven, braided, knit, or otherwise intertwined.

Figure 5A:
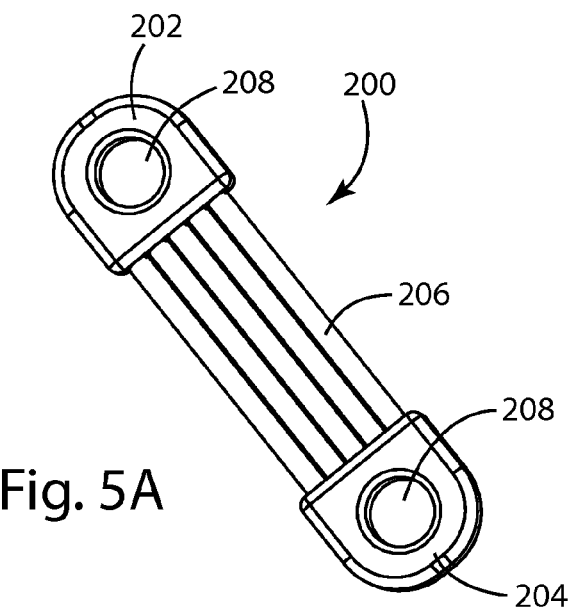
FIG. 5A provides an enlarged perspective view of an elastically deformable bias element of FIG. 1.
Figure 5B:
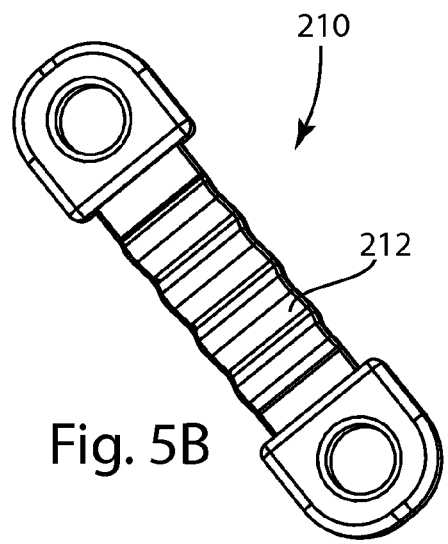
FIG. 5B provides an enlarged perspective view of an alternate embodiment of an elastically deformable bias element.
Figure 5C:
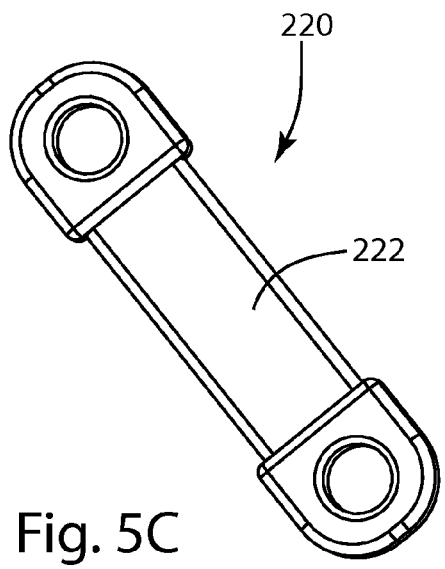
FIG. 5C provides an enlarged perspective view of an alternate embodiment of an elastically deformable bias element.
Figure 5D:
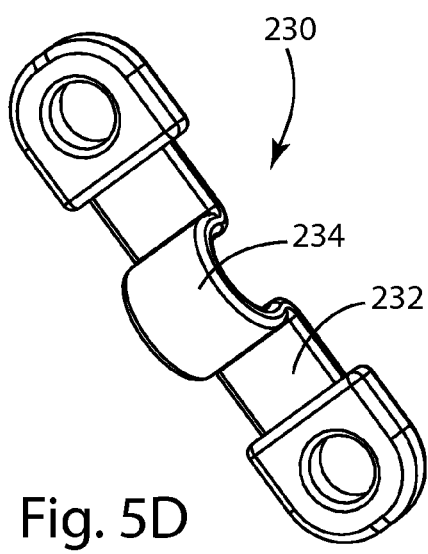
FIG. 5D provides an enlarged perspective view of an alternate embodiment of an elastically deformable bias element.

Referring to FIG. 5B, bias element 210 comprises a bias body 212 having accordion-type folds or pleats. FIG. 5C illustrates a bias element 220 with a substantially flat bias body 222, and FIG. 5D illustrates a bias element 230 having a bias body 232 with a flexure 234. It is appreciated that each material used, and/or configurations of the bias body, may be mixed and matched to provide bias elements with varying degrees of elasticity as necessary for the amount of motion and/or correction desired. In addition to the bias elements depicted, other bias elements within in the scope of the invention may have different cross-sectional geometries as well, such as circular, rectangular, ovoid, annular, or any freeform shape, as well as being solid, hollow, or porous. Also, bias elements may vary in length and/or width to provide varying degrees of elasticity or compliance.

An alternative embodiment of the invention may include at least one bias element which is formed entirely of rigid materials, in order to provide additional motion or balance control constraints on the functional spinal unit, or motion segment, involved. Rigid materials suitable for such a more rigid, less compliant bias element include titanium, stainless steel, aluminum, cobalt chromium, Nitinol, PEEK, and UHMWPE, among others. A rigid bias member may be monolithically formed as one piece, or may include a body portion and fixation portions which are rigidly joined together. A system comprising rigid bias elements coupled between bridge elements may provide a rigid stabilizing force between the bridge elements. It is appreciated that compliant and rigid bias elements may be mixed and matched to achieve the customized needs of the patient in a multi-level procedure. The bias element(s) may be configured to specifically introduce sagittal (lordosis or kyphosis) or coronal balance. Alternatively, or in addition, the bias element(s) may introduce anterior or posterior translation.

Figure 6:
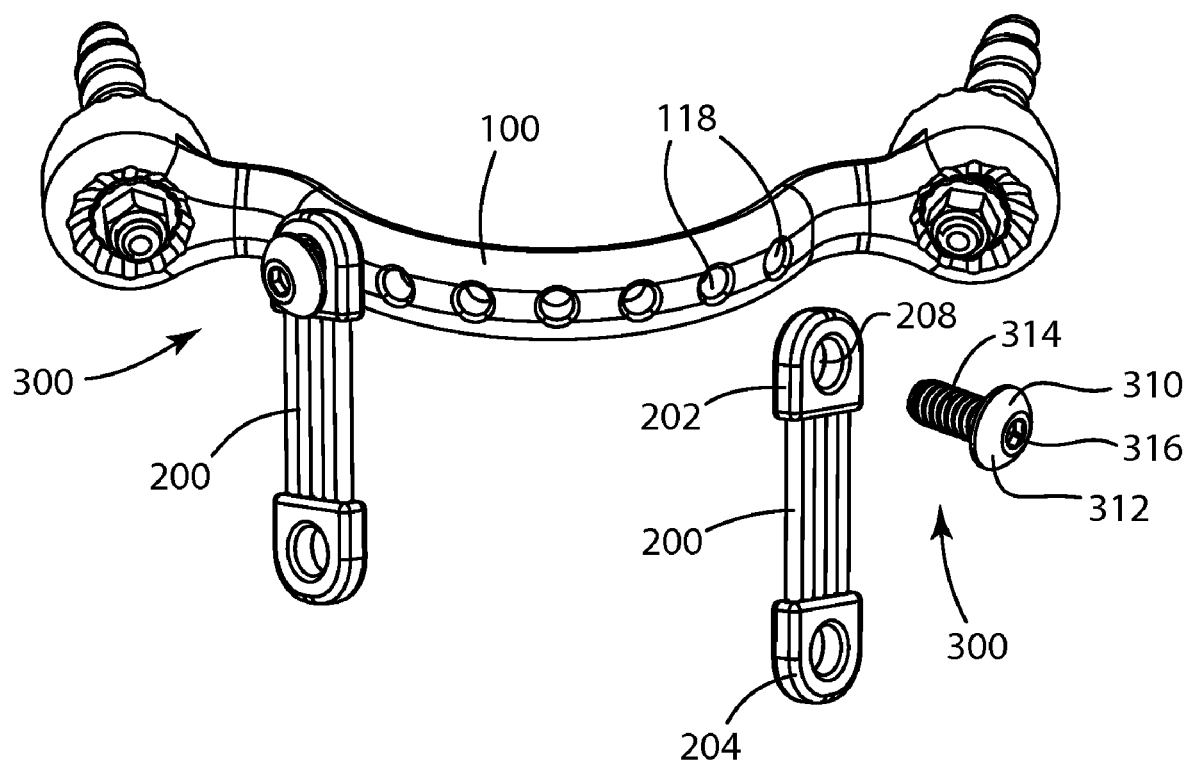
FIG. 6 provides a partially exploded perspective view of a bridge element, two bias elements, two attachment mechanisms and two anchoring members of the dynamic stabilization system of FIG. 1.

Referring to FIG. 6, a partially exploded view shows a bridge element 200 with a bias member 200 attached to the bridge, and an unattached bias member 200 and attachment mechanism 300. In the embodiment depicted, attachment mechanism 300 comprises a screw 310. Screw 310 includes a head portion 312 and a threaded shaft 314. The head portion 312 includes a drive feature 316 which in the example shown is internal; other embodiment may include an external drive feature. To attach the bias member 200 to the bridge element 100, the first fixation portion 202 may be placed adjacent the desired attachment feature 118 such that their respective holes are aligned, then shaft 314 inserted through joining feature 208 and engaged in attachment feature 118. Alternately, the shaft 314 may be inserted through joining feature 208, then screw 310 and bias element 200 are moved together toward the bridge element and the screw 310 engaged with the attachment feature 118 to attach the bias element to the bridge element. The joining feature 208 of the bias element 200 may not be threaded, to allow angular adjustment of the bias element relative to the bridge elements before the position of the bias element is fixed by engaging the attachment mechanism 300 with the attachment feature 118.

Attachment mechanism 300 may be a self-locking screw, or may comprise a locking washer, or backup nut to ensure locking engagement with the bias member and the bridge element, and to prevent unintended backout or removal of the attachment mechanism. It is appreciated that attachment mechanism 300 is removable to provide for revision or adjustment of the bias element relative to the bridge elements. It is also appreciated that other attachment mechanisms exist to secure the bias element to the laminar bridge, including but not limited to clamps, clips, threaded fasteners, posts, holes, press-fits, quick-release and quick-attachment connections, ¼-turn connections, t-slots, dovetail joints, living hinges, and flanged connections.

Referring again to FIGS. 1, 3A and 3B, and 6, system 10 may be implanted as follows. The cervical vertebrae are exposed, and bone anchors 152 are placed with a modified Magerl technique using anatomic landmarks. Laminectomy is then performed following placement of the anchors, and decompression is achieved. Alternatively, laminectomy may first be performed followed by placement of the anchors. Bridge elements 100 are placed over the bone anchors and secured to the resected vertebrae by nuts 154. Two bridge elements 100 may be secured to adjacent vertebrae for single level stabilization, or three or more bridge elements may be used to provide stabilization across multiple levels. Bias elements 200 are attached to the bridge elements via attachment mechanisms 150. Each bias element may be attached to the bridge elements such that it extends essentially perpendicular to the bridge elements, as in FIG. 1, or may be attached in a non-perpendicular position. As bias elements are attached, tension may be applied manually or with a tensioning tool to achieve a desired tension between the bridge elements. Of course, the implantation methods set forth herein may be applied to any of the posterior dynamic stabilization systems or variations disclosed.

Figure 7:
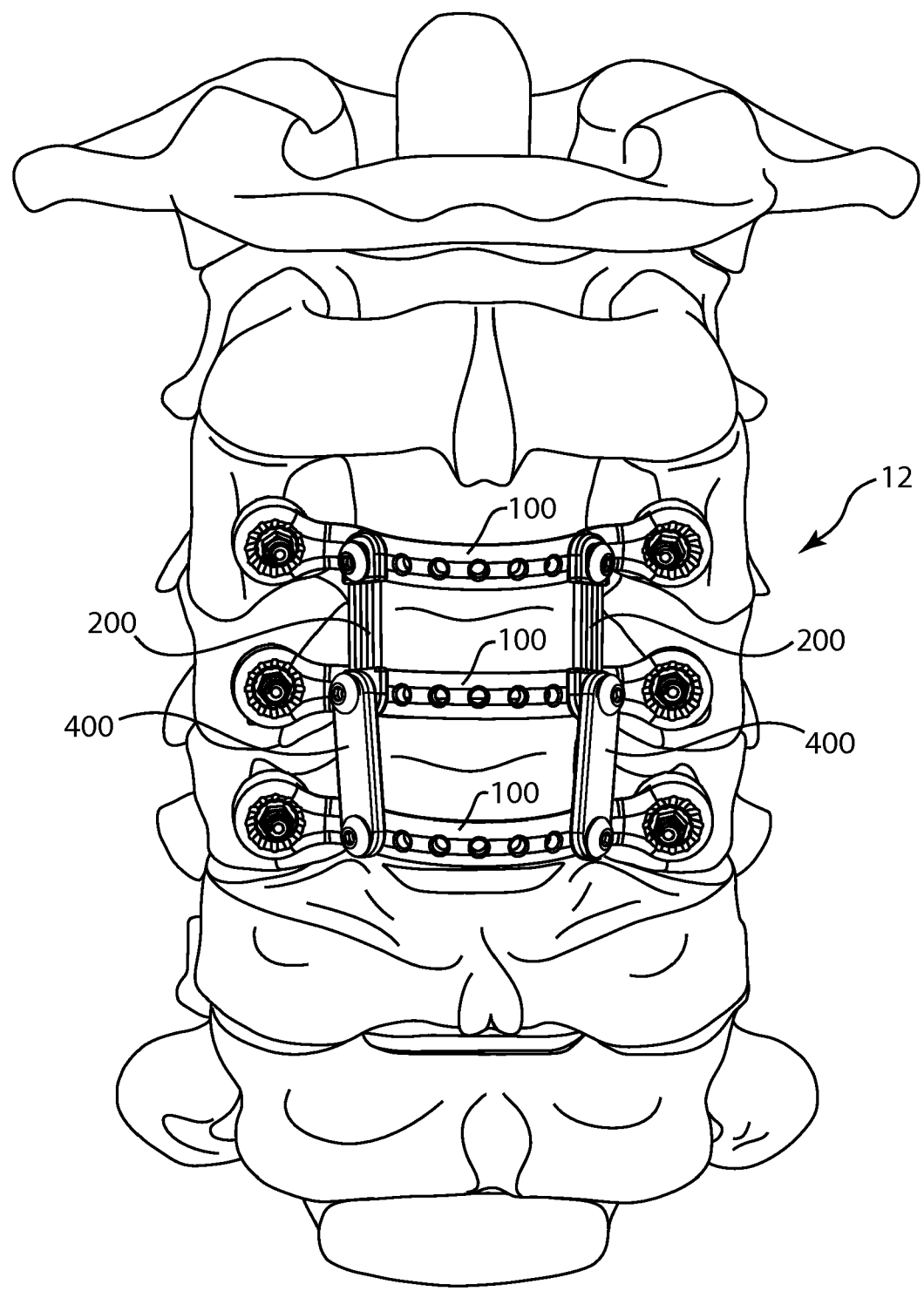
FIG. 7 provides a posterior perspective view of an alternate embodiment of a dynamic stabilization system, comprising two elastically deformable bias elements and two rigid bias elements, anchored to a portion of a spine.

FIGS. 7-14 show alternative embodiments of posterior dynamic stabilization systems. In FIG. 7, system 12 comprises three bridge elements 100 secured to three respective vertebrae. Elastically deformable bias elements 200 are secured bilaterally between the first and second bridge elements, to provide dynamic stabilization at that vertebral level. Rigid bias elements 400 are secured bilaterally to the second and third bridge elements, to provide rigid stabilization at that vertebral level. Another alternative embodiment could include elastically deformable bias elements secured to bridges at one vertebral level, and different elastically deformable bias elements with a lower or higher degree of elasticity, at a second vertebral level.

Figure 8:
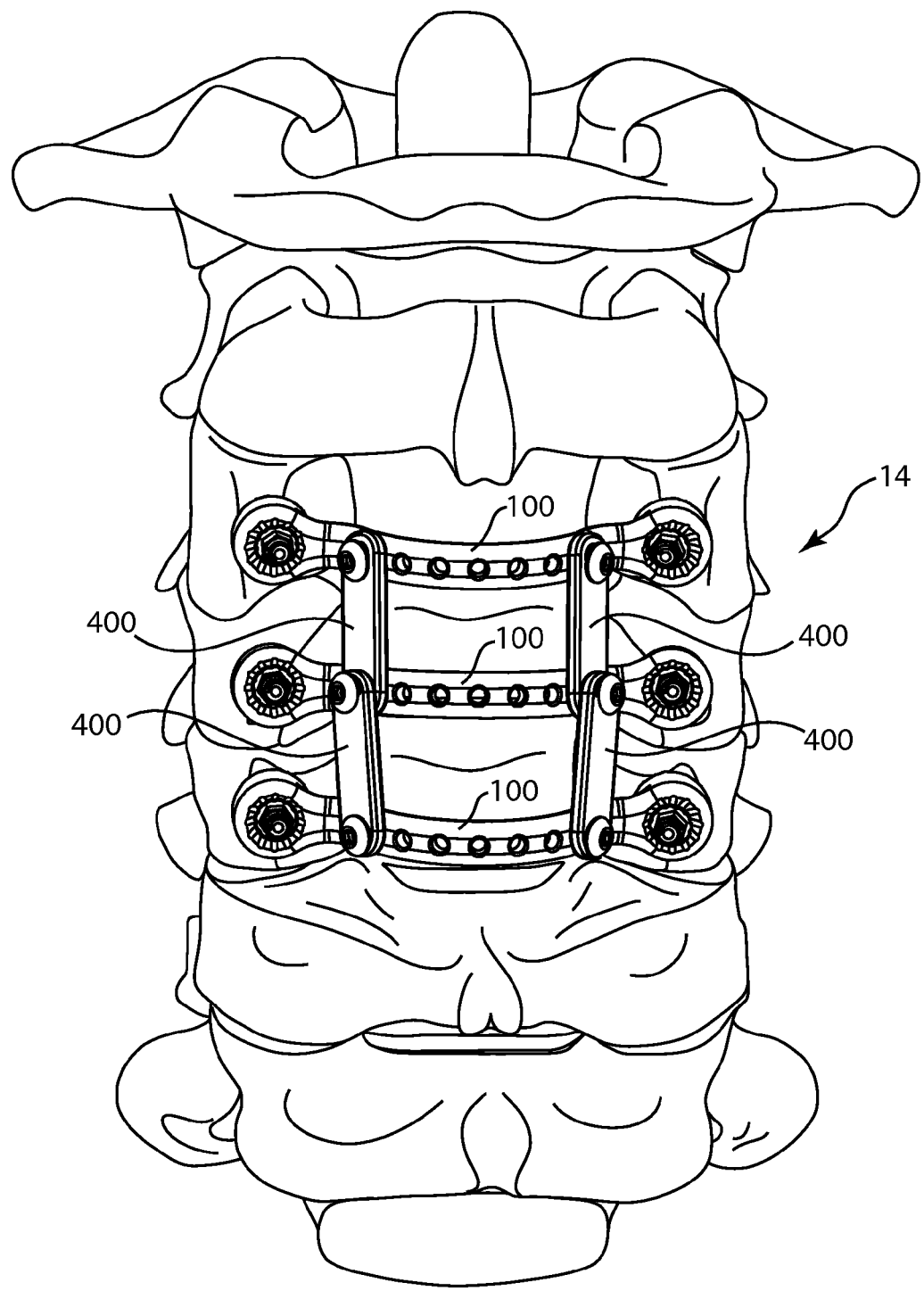
FIG. 8 provides a posterior perspective view of an alternate embodiment of a stabilization system, comprising four bias elements, anchored to a portion of a spine.

Referring to FIG. 8, system 14 comprises three bridge elements 100 secured to three respective vertebrae. Rigid bias elements 400 are secured bilaterally to the first and second bridge elements and to the second and third bridge elements, to provide rigid stabilization at both vertebral levels. In an alternative embodiment of system 14, the bridge elements may comprise elastically deformable material while the bias elements comprise rigid material, to provide dynamic stabilization at both vertebral levels.

Figure 9:
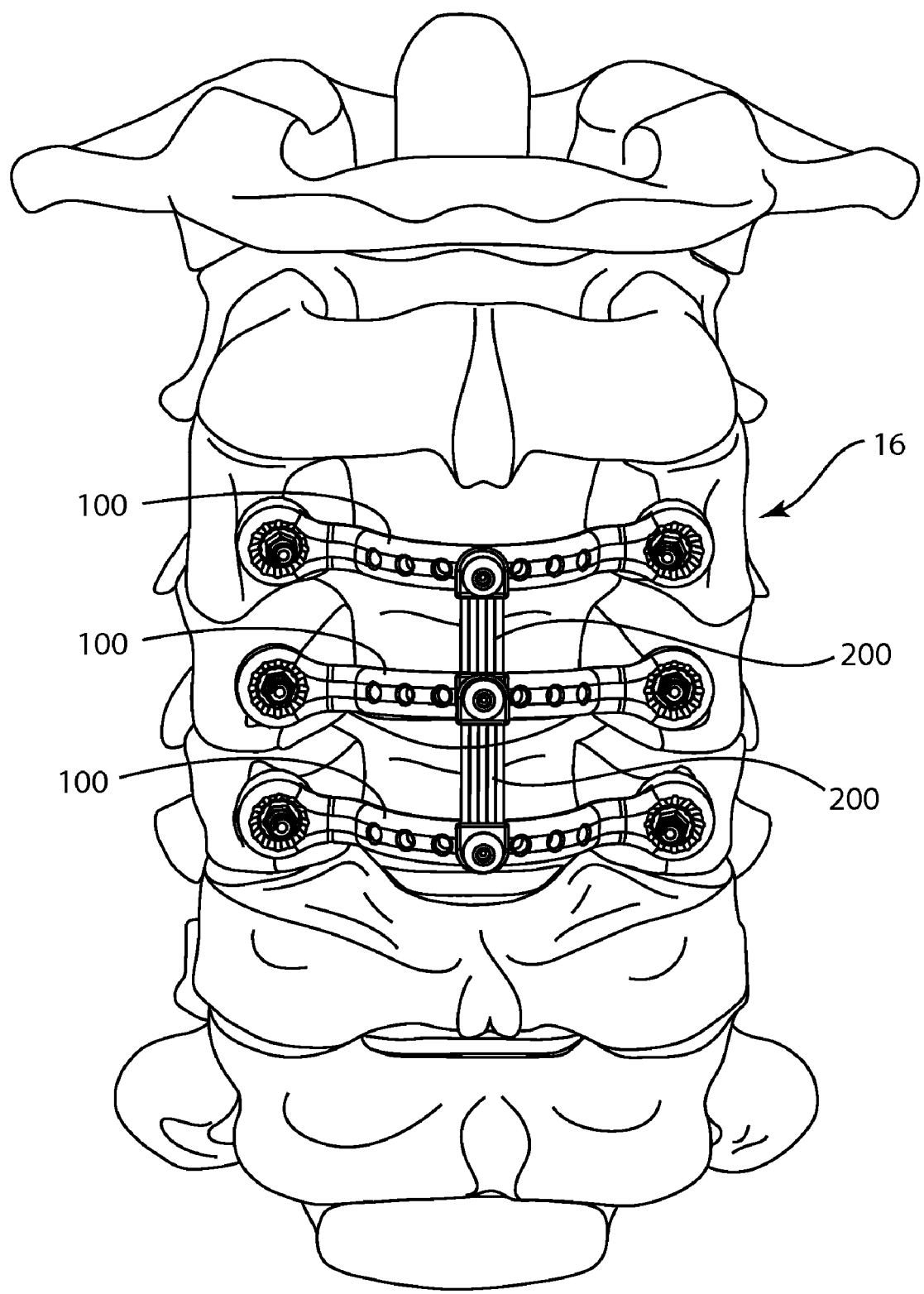
FIG. 9 provides a posterior perspective view of an alternate embodiment of a dynamic stabilization system, comprising two bias elements attached to bridge elements at the vertebral midline, anchored to a portion of a spine.

Referring to FIG. 9, system 16 comprises three bridge elements 100 secured to three respective vertebrae. An elastically deformable bias element 200 is attached to the first and second bridge elements, aligned with the midline or sagittal plane of the vertebrae and the bridge elements. A second elastically deformable bias element 200 is attached to the second and third bridge elements, and is also aligned with the midline or sagittal plane of the vertebrae and the bridge elements. It is appreciated that the second deformable bias element may have the same, or different, elasticity as the first bias element. Another alternative embodiment could include rigid bias elements 400 aligned along the midline or sagittal plane at one or both vertebral levels.

Figure 10:
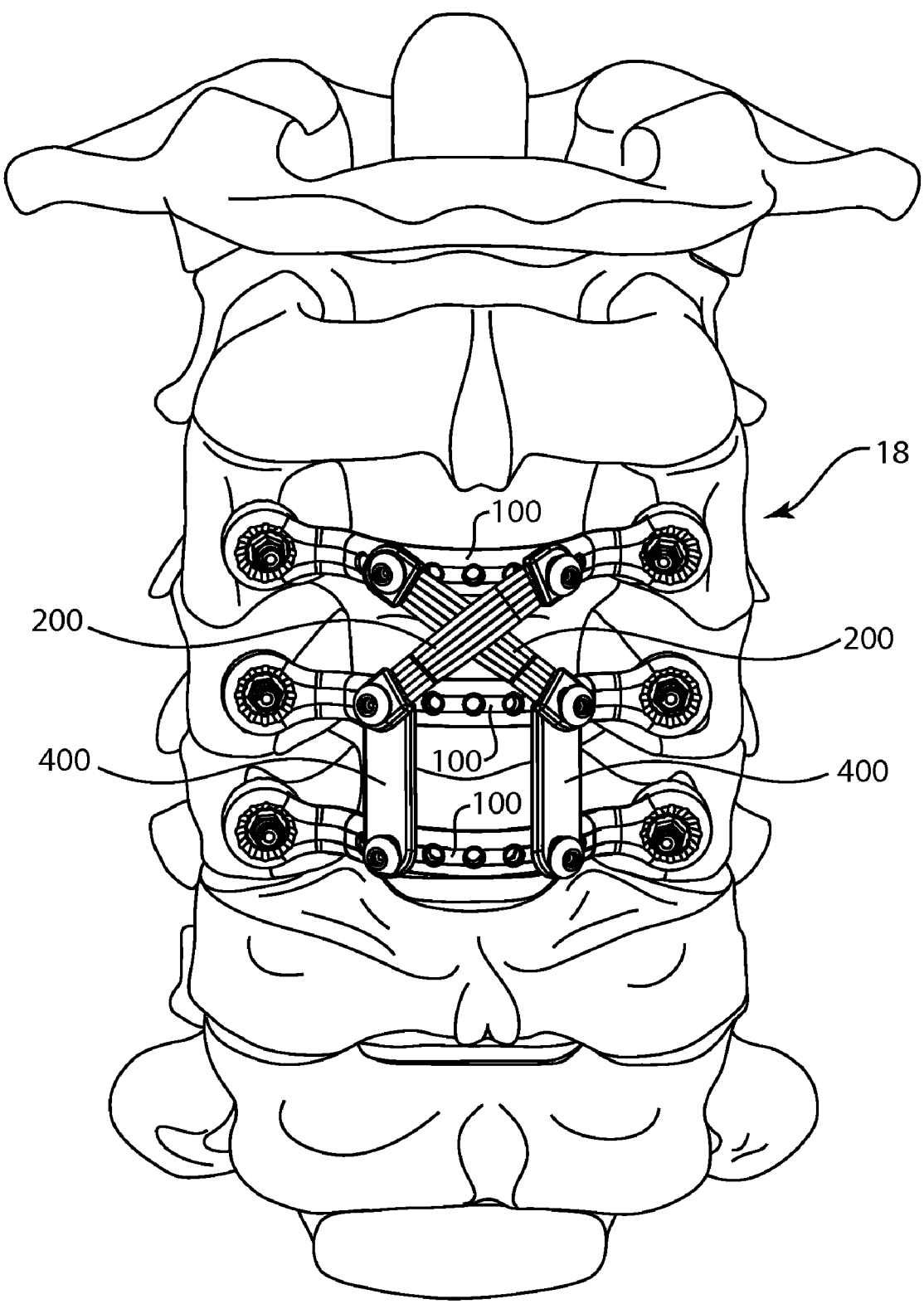
FIG. 10 provides a posterior perspective view of an alternate embodiment of a dynamic stabilization system, comprising two elastically deformable bias elements attached to cross each other at one vertebral level, and two rigid bias elements at a second vertebral level, anchored to a portion of a spine.

Referring to FIG. 10, system 18 comprises three bridge elements 100 secured to three respective vertebrae. A cephalad end of an elastically deformable bias element 200 is attached to the first bridge element, and a caudal end is attached to the second bridge element at a location medial-laterally offset from the first location. A second elastically deformable bias element 200 is attached in an opposite manner, so that the second bias element crosses over the first bias element. Such a configuration may aid in maintaining patient balance and/or correcting deformities in the sagittal and/or coronal planes. Two rigid bias elements extend between the second and third bridge elements to provide rigid stabilization at that level.

Figure 11:
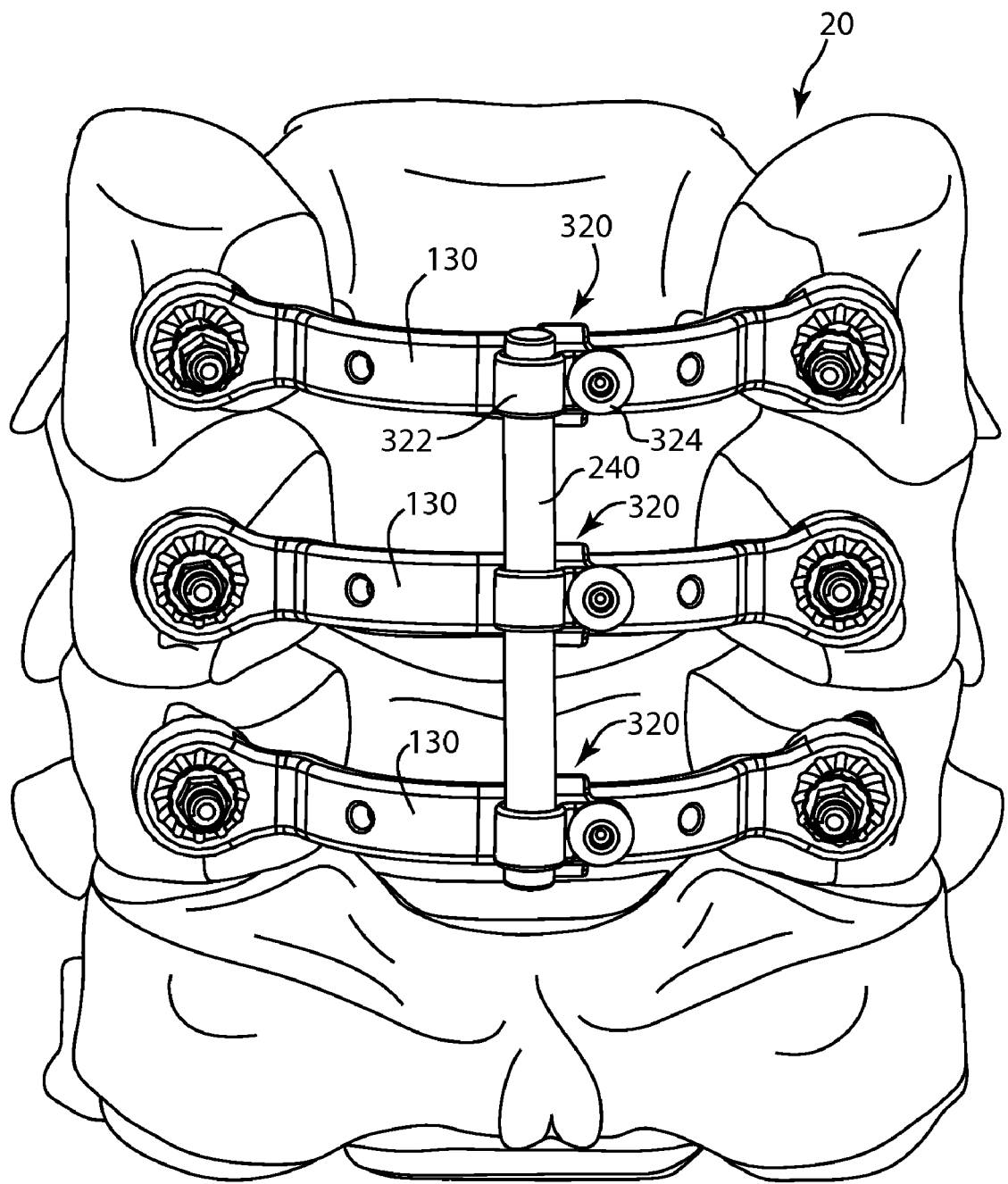
FIG. 11 provides a posterior perspective view of an alternate embodiment of a dynamic stabilization system comprising a bias element extending across two vertebral levels, anchored to a portion of a spine.

FIGS. 11-14 depict posterior dynamic stabilization systems which each include a continuous length of elastically deformable material which is attached across two vertebral levels. Referring to FIG. 11, system 20 comprises three bridge elements 130, each of which is oriented medial-laterally across a vertebra and secured to the vertebra via two anchoring members. A bias element 240 extends across all three bridge elements at a midline or sagittal position, and is coupled to each bridge element by an attachment mechanism 320. Attachment mechanism 320 comprises a clamp 322 and a screw 324. The screw engages the clamp and the bridge element to both attach the clamp to the bridge element and attach the bias element to the clamp at a desired tension.

Figure 12A:
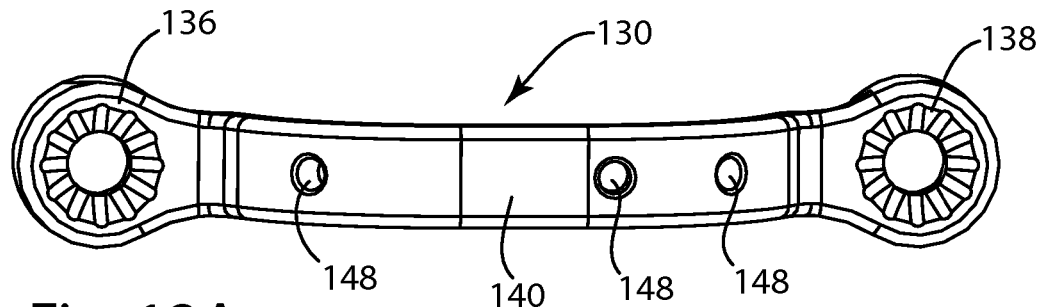
FIG. 12A provides a posterior perspective view of a bridge element of the dynamic stabilization system of FIG. 11.
Figure 12B:
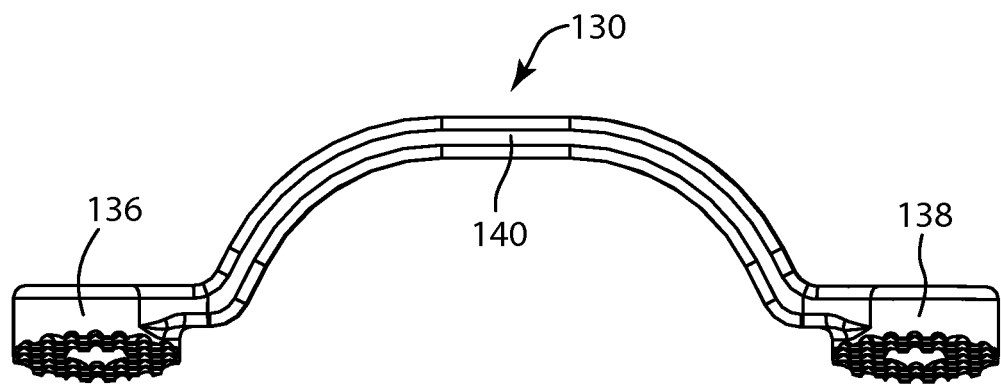
FIG. 12B provides a caudal perspective view of the bridge element of FIG. 12A.

Bridge element 130 is shown in FIGS. 12A and 12B. Bridge 130 comprises a first end having an anchoring feature 136, and a second end having an anchoring feature 138. A plurality of individual discretely located attachment features 148 are distributed along a bridge body 140. The attachment features, which may be threaded to engage corresponding threads on an attachment mechanism, may be distributed evenly or unevenly along the bridge body. In comparison with bridge element 100 as seen in FIG. 2C, it can be seen that the bridge body 140 of bridge element 130 is flatter than bridge body 110 of bridge element 100. This flatter configuration helps to compensate for the anterior-posterior dimension of the clamp in order to provide a suitably low profile implant.

Figure 12C:
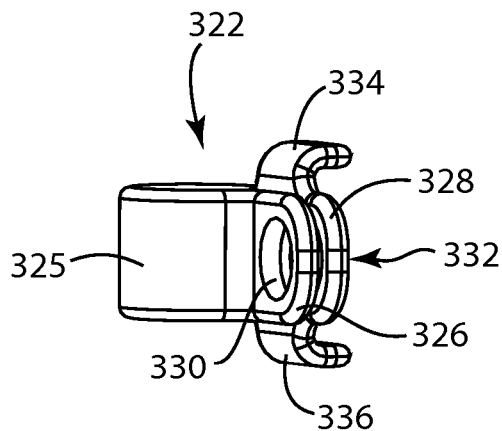
FIG. 12C a perspective view of a clamp of the dynamic stabilization system of FIG. 11.
Figure 12D:
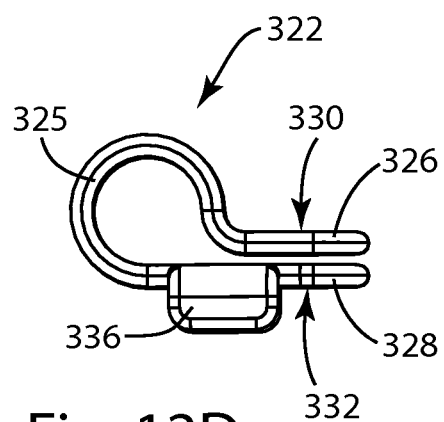
FIG. 12D provides a perspective view of the clamp of FIG. 12C.

FIG. 12C depicts a medial perspective view of clamp 322, and FIG. 12D depicts a caudal view of the clamp. The clamp 322 comprises an open loop portion 325 sized to receive a portion of bias material. A first tab 326 and a second tab 328 are continuations of the loop portion 325. Tab 326 has an opening 330, and tab 328 has an opening 332, and the tabs are positioned relative to one another such that the openings are concentrically aligned. Two stops 334, 336 extend from tab 328. When the clamp is positioned on a bridge element body 140 as in FIG. 11, the stops 334, 336 project on either side of the bridge body and may prevent rotation of the clamp relative to the bridge body. Openings 330, 332 are sized and shaped to receive a shaft of screw 324. As seen in FIG. 11, clamp 322 is positionable on a bridge element at an attachment feature 148, with stops 334, 336 positioned on either cephalad/caudal side of the bridge element. Bias element 240 is insertable through the loop portion 325. Screw 324 is insertable through clamp openings 330, 332 and into the attachment feature 148. When screw 324 is tightened, loop portion 325 closes around bias element 240, and clamp 322 is rigidly attached to the bridge element, unable to rotate or translate. It is also appreciated that other attachment mechanisms exist to secure the bias element to the bridge, including but not limited to clamps, clips, threaded fasteners, posts, holes, press-fits, quick-release and quick-attachment connections, ¼-turn connections, t-slots, dovetail joints, living hinges, and flanged connections.

Bias element 240 may comprise a single piece or multiple pieces of an elastically deformable material. The material composition, length, width, and/or elasticity of bias element 240 may vary as needed to attain the desired tension for balance control, deformity correction or other desired outcome.

Figure 13:
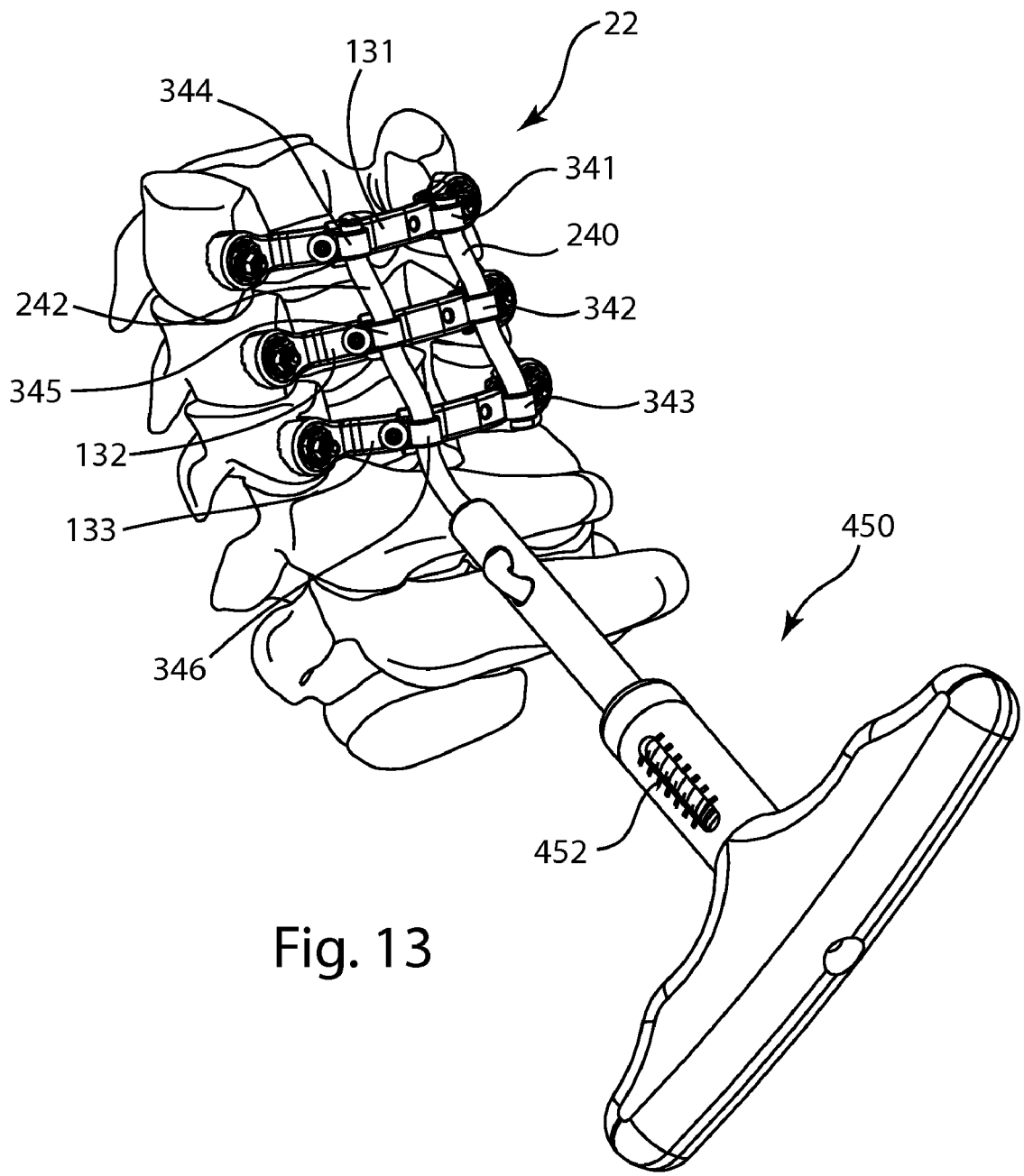
FIG. 13 provides a perspective view of an alternate embodiment of a dynamic stabilization system comprising two elastically deformable bias elements extending across two vertebral levels, anchored to a portion of a spine, and a tensioning tool.

Referring to FIG. 13, posterior dynamic stabilization system 22 comprises three bridge elements 131, 132, and 133, bias elements 240 and 242, assembled with a plurality of anchoring members and attachment mechanisms. Attachment mechanisms 341, 342, 343, 344, 345 and 346 may each comprise an attachment mechanism 320. Bias element 240 has been tensioned and attached to the three bridge elements by attachment mechanisms 341, 342, 343 to provide tension at two vertebral levels. Bias element 242 comprises a length of elastically deformable material. During an implantation process, bias element 242 may be inserted through the loop portions of attachment mechanisms 344, 345, 346. The attachment mechanism 344 on bridge element 131 may be tightened to firmly hold the bias element 242. A tensioning tool 450 may be coupled to a portion of the bias element, and actuated to provide tension to the bias element. The tensioning tool 450 comprises a spring 452, the tool configured such that deflection of the spring provides tension to the bias element. The spring deflection may be viewed through a window or slot in the tool and a measurement scale may be present on the tool to indicate the magnitude of tension on the bias element. When a desired tension is attained, the attachment mechanism 345 on bridge element 132 may be tightened to lock down the bias element 242 at the desired tension. Finally, the tension on bias element 242 may be adjusted between bridge element 132 and 133 by actuation of the tensioning tool, and attachment mechanism 346 tightened to lock down the bias element 242 at the desired tension. Bias element 242 may then be severed between attachment mechanism 346 and the tensioning tool. It is appreciated that bias element may be attached in the same manner as bias element 242, and that the bias elements 240, 242 can be inserted, tensioned and locked down in a cephalad-to-caudal order, or vice versa. It is also appreciated that a third bias element may be added to the system to provide additional dynamic support if desired.

Figure 14:
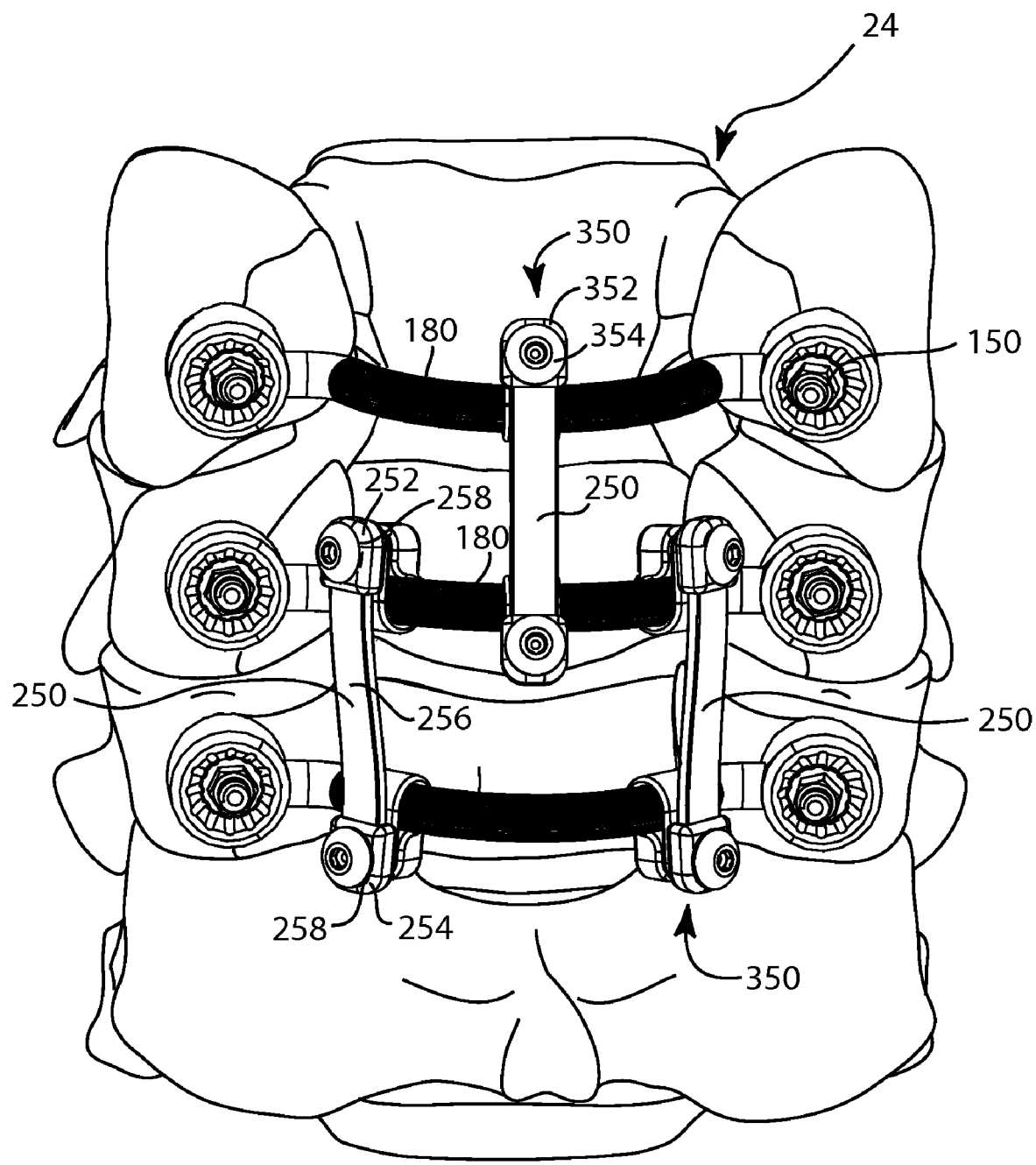
FIG. 14 provides a posterior perspective view of an alternate embodiment of a dynamic stabilization system, anchored to a portion of a spine.

Another alternative embodiment of a posterior dynamic stabilization system is shown in FIG. 14. System 24 comprises three bridge elements 180, each secured in a medial-lateral orientation to a vertebra by anchoring members 150. A single bias element 250 is attached to first and second bridge elements 180 in a midline position. Two additional bias elements 250 are attached to the second and third bridge elements in a bilateral arrangement. Attachment mechanisms 350, which comprise clamp 352 and screw 354, attach the bias elements 250 to the bridge elements 180. Each bias element 250 comprises a first fixation portion 252, a second fixation portion 254, and a bias body 256, and each fixation portion comprises a joining feature 258.

FIGS. 15A-15D show the details of bridge element 180 and clamp 352. Bridge element 180 comprises a first end 182 having an anchoring feature 184, and a second end 186 having an anchoring feature 188. Bridge body 190 has a circular cross-section, and an outer connection surface 192. In the embodiment depicted, the connection surface 192 is ridged in order to promote a non-slipping grip connection between the bridge body and the attachment mechanism(s) 340. In alternative embodiments, connection surface 192 may comprise other gripping features such as knurling, longitudinal grooves, facets, nubs, and combinations thereof, and/or include surface treatments, roughening or excoriation. The attachment mechanisms 350 can be attached to the bridge element 180 at any location along the bridge body 190, thus providing a plurality of continuous non-discrete attachment locations. This configuration allows the practitioner to select the precise attachment location needed to produce the desired result, whether it is balance control, deformity correction or a combination.

As seen in FIGS. 15C and 15D, clamp 352 comprises an open loop portion 356 sized to surround a portion of a bridge body 190. A first tab 358 and a second tab 360 are continuations of the loop portion 356. Tab 358 has an opening 362, and tab 360 has an opening 364, and the tabs are positioned relative to one another such that the openings are axially aligned. Openings 362, 364 are sized and shaped to receive a shaft of screw 354. As seen in FIG. 14, clamp 352 is positionable on a bridge body 180 at any non-discrete location along the body. One joining feature 258 of a bias element 250 may be placed adjacent the openings 362, 364 of the clamp 352. Screw 354 is insertable through the joining feature 258 and the clamp openings 362, 364. When screw 354 is tightened, loop portion 356 closes around the bridge body 190, and clamp 352 is rigidly attached to the bridge element. Prior to tightening, clamp 352 may be rotated about the bridge body 190 to a desired position. This rotation allows for tension adjustment of the bias element 250 between the two bridge elements 180. Of course, during the implantation process, the positions of the attachment mechanisms along the lengths of bridge bodies may be adjusted, as can the rotational position of the attachment mechanism, by loosening the screw 354, making the desired adjustment(s), and re-tightening the screw. The second joining feature of bias element 250 is attached to a second bridge 180 in a similar fashion. It is also appreciated that other attachment mechanisms exist to secure the bias element to the bridge, including but not limited to clamps, clips, threaded fasteners, locking nuts, posts, holes, press-fits, quick-release and quick-attachment connections, ¼-turn connections, t-slots, dovetail joints, living hinges, and flanged connections.

The present invention may be embodied in other specific forms without departing from its spirit or essential characteristics. For example, above are described various alternative examples of systems for providing posterior dynamic stabilization. It is appreciated that various features of the above-described examples can be mixed and matched to form a variety of other alternatives. For example, elastically deformable and rigid bias elements may be used in combination or separately. The bias elements may be placed parallel to one another and perpendicular to the bridging elements, or non-parallel and/or non-perpendicular. It is also appreciated that this system should not be limited to the cervical spine, and may be used on any portion of the spine. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A spinal stabilization implant for attachment to a portion of a spine, the implant comprising:
   a first bridge element comprising a first bridge end having a first anchoring feature, a second bridge end having a second anchoring feature, and a first bridge body extending between the first and second bridge ends, the first bridge element sized and shaped for securing to a vertebra in a medial-lateral orientation;
   a second bridge element comprising a third bridge end having a third anchoring feature, a fourth bridge end having a fourth anchoring feature, and a second bridge body extending between the third and fourth bridge ends, the second bridge element sized and shaped for securing to a vertebra in a medial-lateral orientation;
   a plurality of anchoring members, wherein a first anchoring member interfaces with the first anchoring feature for securing the first bridge end to a first vertebra, a second anchoring member interfaces with the second anchoring feature for securing the second bridge end to the first vertebra, a third anchoring member interfaces with the third anchoring feature for securing the third bridge end to a second vertebra, and a fourth anchoring member interfaces with the fourth anchoring feature for securing the fourth bridge end to the second vertebra;
   a first bias element that attaches to the first bridge element and the second bridge element to provide a stabilizing force between the bridge elements when the bridge elements are properly secured to two respective vertebrae, wherein the first bias element comprises a cephalad fixation portion removably attachable to the first bridge element, a caudal fixation portion removably attachable to the second bridge element, and a bias body extending between the cephalad and caudal fixation portions, wherein the cephalad and caudal fixation portions attach to the corresponding bridge element at any one of a plurality of discrete attachment locations; and
   a plurality of attachment mechanisms, wherein each attachment mechanism comprises a attachment portion for interfacing with a bias element to attach the bias element to one of the bridge elements, wherein the cephalad and caudal fixation portions each attach at any one of the plurality of discrete attachment locations with one of the attachment mechanisms, wherein the attachment mechanism further comprises a clamp and a screw, the attachment mechanism positionable such that the clamp at least partially surrounds one of the bridge elements, wherein tightening the screw secures the first bias element to the attachment mechanism and locks the position of the attachment mechanism relative to the bridge element.

2. The implant of claim 1, further comprising:
a third bridge element, comprising a fifth bridge end having a fifth anchoring feature, a sixth bridge end having a sixth anchoring feature, and a third bridge body extending between the fifth and sixth bridge ends, the third bridge element sized and shaped for securing to a vertebra in a medial-lateral orientation, the third bridge element between the first and second bridge elements,
wherein the first bias element further comprises a middle portion between the cephalad end and the caudal end, wherein the middle portion interfaces with one of the attachment mechanisms to attach the middle portion to the third bridge element.

3. The implant of claim 1, wherein the first bias element comprises an elastically deformable member formed from material chosen from the group consisting of elastomers, silicones, urethanes, bio-absorbable materials, woven textile structures, knit textile structures, braided textile structures, molded thermoplastic polymers, ethylene-vinyl acetate, PEEK, UHMWPE, nitinol, titanium and stainless steel, wherein the first bias element provides a dynamic stabilizing force between the bridge elements.

4. The implant of claim 3, wherein the cephalad and caudal fixation portions are formed of a rigid material, and wherein the bias body consists of the elastically deformable material.

5. The implant of claim 1 wherein the first bias element is formed of a rigid material selected from the group consisting of titanium, stainless steel, aluminum, cobalt chromium, Nitinol, PEEK, and UHMWPE, wherein the first bias element provides a rigid stabilizing force between the bridge elements.

6. The implant of claim 1, wherein the first bias element removably attaches to the bridge elements such that the first bias element extends substantially perpendicular to the bridge elements.

7. The implant of claim 6, wherein the cephalad fixation portion of the first bias element attaches to the first bridge element and the caudal end of the first bias element attaches to the second bridge element such that the first bias element is substantially parallel to the sagittal plane.

8. The implant of claim 1, further comprising:
a second bias element comprising a cephalad fixation portion, a caudal fixation portion and a bias body extending between the cephalad and caudal fixation portions, wherein the cephalad fixation portion attaches to the first bridge element at any of a plurality of attachment locations, and wherein the caudal fixation portion attaches to the second bridge element at any of a plurality of attachment locations.

9. The implant of claim 8, wherein the first bias element comprises an elastically deformable material to provide an dynamic stabilizing force between the first and second bridge elements, and wherein the second bias element is formed of a rigid material to provide a rigid stabilizing force between the second and third bridge elements.

10. The implant of claim 1, further comprising:
a third bridge element comprising a fifth bridge end having an fifth anchoring feature, a sixth bridge end having a sixth anchoring feature, and a third bridge body extending between the fifth and sixth bridge ends, the third bridge element sized and shaped for securing to a vertebra in a medial-lateral orientation; and
a second bias element;
wherein the second bias element attaches to the second bridge element and to the third bridge element to provide a stabilizing force between the second and third bridge elements when the bridge elements are properly secured to three respective vertebrae.

11. The implant of claim 1, wherein the first and second bridge elements each comprise an elastically deformable material, and wherein the first bias element is formed of a rigid material.

12. A spinal stabilization implant for attachment to a portion of a spine, the implant comprising:
a first bridge element comprising a first bridge end having a first anchoring feature, a second bridge end having a second anchoring feature, and a first bridge body extending between the first and second bridge ends, the first bridge element sized and shaped for securing to a vertebra in a medial-lateral orientation;
a second bridge element comprising a third bridge end having a third anchoring feature, a fourth bridge end having a fourth anchoring feature, and a second bridge body extending between the third and fourth bridge ends, the second bridge element sized and shaped for securing to a vertebra in a medial-lateral orientation;
a plurality of anchoring members, wherein a first anchoring member interfaces with the first anchoring feature for securing the first bridge end to a first vertebra, a second anchoring member interfaces with the second anchoring feature for securing the second bridge end to the first vertebra, a third anchoring member interfaces with the third anchoring feature for securing the third bridge end to a second vertebra, and a fourth anchoring member interfaces with the fourth anchoring feature for securing the fourth bridge end to the second vertebra; and
a first bias element that attaches to the first bridge element and the second bridge element to provide a stabilizing force between the bridge elements when the bridge elements are properly secured to two respective vertebrae,
wherein the first bias element comprises a cephalad fixation portion removably attachable to the first bridge element, a caudal fixation portion removably attachable to the second bridge element, and a bias body extending between the cephalad and caudal fixation portions,
wherein each anchoring feature comprises an aperture and each anchoring member comprises a screw sized and shaped to be received in the aperture, wherein each screw is individually polyaxially positionable relative to the anchoring feature when the screw is received in the aperture.

13. The implant of claim 12, further comprising:
a plurality of attachment mechanisms, wherein each attachment mechanism comprises a attachment portion for interfacing with a bias element to attach the bias element to one of the bridge elements.

14. The implant of claim 13, wherein the cephalad and caudal fixation portions each attach at any one of a plurality of attachment locations with one of the attachment mechanisms, wherein the attachment mechanism further comprises a clamp and a screw, the attachment mechanism positionable such that the clamp at least partially surrounds one of the bridge elements, wherein tightening the screw secures the first bias element to the attachment mechanism and locks the position of the attachment mechanism relative to the bridge element.

15. The implant of claim 13, wherein the cephalad and caudal fixation portions are attachable at any one of a plurality of discrete attachment locations with one of the attachment mechanisms, wherein the attachment mechanism further comprises a screw, wherein each bridge element comprises at least one hole extending through the bridge element, the hole sized and shaped to receive the screw; and
    wherein the attachment mechanism is positionable such that tightening the screw secures the bias element to the attachment mechanism and locks the position of the attachment mechanism relative to the bridge element.

16. The implant of claim 14, wherein each bridge body comprises a circular cross-section having a connection surface comprising a gripping feature, wherein the attachment mechanism is positionable such that the clamp at least partially surrounds one of the bridge bodies, wherein tightening the screw secures the first bias element to the attachment mechanism and locks the position of the attachment mechanism relative to the bridge body.

17. The implant of claim 12, further comprising:
    a third bridge element, comprising a fifth bridge end having a fifth anchoring feature, a sixth bridge end having a sixth anchoring feature, and a third bridge body extending between the fifth and sixth bridge ends, the third bridge element sized and shaped for securing to a vertebra in a medial-lateral orientation, the third bridge element between the first and second bridge elements,
    wherein the first bias element further comprises a middle portion between the cephalad end and the caudal end, wherein the middle portion attaches to the third bridge element.

18. The implant of claim 12, wherein the first bias element comprises an elastically deformable member formed from material chosen from the group consisting of elastomers, silicones, urethanes, bio-absorbable materials, woven textile structures, knit textile structures, braided textile structures, molded thermoplastic polymers, ethylene-vinyl acetate, PEEK, UHMWPE, nitinol, titanium and stainless steel, wherein the first bias element provides a dynamic stabilizing force between the bridge elements.

19. The implant of claim 18, wherein the cephalad and caudal fixation portions are formed of a rigid material, and wherein the bias body consists of the elastically deformable material.

20. The implant of claim 12 wherein the first bias element is formed of a rigid material selected from the group consisting of titanium, stainless steel, aluminum, cobalt chromium, Nitinol, PEEK, and UHMWPE, wherein the first bias element provides a rigid stabilizing force between the bridge elements.

21. The implant of claim 12, wherein the first bias element removably attaches to the bridge elements such that the first bias element extends substantially perpendicular to the bridge elements.

22. The implant of claim 12, further comprising:
    a second bias element comprising a cephalad fixation portion, a caudal fixation portion and a bias body extending between the cephalad and caudal fixation portions, wherein the cephalad fixation portion attaches to the first bridge element at any of a plurality of attachment locations, and wherein the caudal fixation portion attaches to the second bridge element at any of a plurality of attachment locations.

23. The implant of claim 22, wherein the cephalad fixation portion of the first bias element attaches to the first bridge element at a first location and the caudal fixation portion of the first bias element attaches to the second bridge element at a second location medial-laterally offset from the first location;
    wherein the cephalad fixation portion of the second bias element attaches to the first bridge element at a third location and the caudal fixation portion of the second bias element attaches to the second bridge element at a fourth location medial-laterally offset from the third location such that the second bias element crosses over or under the first bias element.

24. The implant of claim 12, further comprising:
    a third bridge element comprising a fifth bridge end having a fifth anchoring feature, a sixth bridge end having a sixth anchoring feature, and a third bridge body extending between the fifth and sixth bridge ends, the third bridge element sized and shaped for securing to a vertebra in a medial-lateral orientation; and
    a second bias element;
    wherein the second bias element attaches to the second bridge element and to the third bridge element to provide a stabilizing force between the second and third bridge elements when the bridge elements are properly secured to three respective vertebrae.

25. The implant of claim 24, wherein the first bias element comprises an elastically deformable material to provide an dynamic stabilizing force between the first and second bridge elements, and wherein the second bias element is formed of a rigid material to provide a rigid stabilizing force between the second and third bridge elements.

26. A spinal stabilization implant for attachment to a portion of a spine, the implant comprising:
    a first bridge element comprising a first bridge end having a first anchoring feature, a second bridge end having a second anchoring feature, and a first bridge body extending between the first and second bridge ends, the first bridge element sized and shaped for securing to a vertebra in a medial-lateral orientation;
    a second bridge element comprising a third bridge end having a third anchoring feature, a fourth bridge end having a fourth anchoring feature, and a second bridge body extending between the third and fourth bridge ends, the second bridge element sized and shaped for securing to a vertebra in a medial-lateral orientation;
    a plurality of anchoring members, wherein a first anchoring member interfaces with the first anchoring feature for securing the first bridge end to a first vertebra, a second anchoring member interfaces with the second anchoring feature for securing the second bridge end to the first vertebra, a third anchoring member interfaces with the third anchoring feature for securing the third bridge end to a second vertebra, and a fourth anchoring member interfaces with the fourth anchoring feature for securing the fourth bridge end to the second vertebra; and
    an elastically deformable first bias element that attaches to the first bridge element and the second bridge element to provide a dynamic stabilizing force between the bridge elements when the bridge elements are properly secured to two respective vertebrae, the first bias element comprising a first fixation portion, a second fixation portion and a bias body extending between the first and second fixation portions;
    wherein the first fixation portion attaches to the first bridge element at a location medially offset from the first and second anchor features, wherein the second fixation portion attaches to the second bridge element at a location medially offset from the third and fourth anchor features, and wherein the first and second fixation portions removably attach to the corresponding bridge element at any one of a plurality of discrete attachment locations.

27. The implant of claim 26, further comprising:
a plurality of attachment mechanisms, wherein each attachment mechanism comprises a attachment portion for interfacing with a bias element to attach the bias element to one of the bridge elements.

28. The implant of claim 27, wherein each attachment mechanism further comprises a screw, the attachment mechanism positionable such that tightening the screw secures the bias element to the attachment mechanism and locks the position of the attachment mechanism relative to the bridge element.

29. The implant of claim 27, further comprising:
a third bridge element, comprising a fifth bridge end having a fifth anchoring feature, a sixth bridge end having a sixth anchoring feature, and a third bridge body extending between the fifth and sixth bridge ends, the third bridge element sized and shaped for securing to a vertebra in a medial-lateral orientation, the third bridge element between the first and second bridge elements,
wherein the first bias element further comprises a middle portion between the first fixation portion and the second fixation portion, wherein the middle portion interfaces with an attachment mechanism to attach the middle portion to the third bridge element.

30. The implant of claim 27, wherein the first and second fixation portions are attachable at any one of the plurality of discrete attachment locations with one of the attachment mechanisms, wherein the attachment mechanism further comprises a screw, wherein each bridge element comprises at least one hole extending through the bridge element, the hole sized and shaped to receive the screw; and
wherein the attachment mechanism is positionable such that tightening the screw locks the position of the attachment mechanism relative to the bridge element.

31. The implant of claim 26, wherein the first bias element comprises an elastically deformable member formed from material chosen from the group consisting of elastomers, silicones, urethanes, bio-absorbable materials, woven textile structures, knit textile structures, braided textile structures, molded thermoplastic polymers, ethylene-vinyl acetate, PEEK, UHMWPE, nitinol, titanium, and stainless steel, wherein the first bias element provides a dynamic stabilizing force between the bridge elements.

32. The implant of claim 31, wherein the first and second fixation portions are formed of a rigid material, wherein the bias body consists of the elastically deformable material.

33. The implant of claim 26, wherein the first bias element is removably attachable to the bridge elements such that the first bias element extends substantially perpendicular to the bridge elements.

34. The implant of claim 26, further comprising:
a second bias element comprising a first fixation portion, a second fixation portion end and a bias body extending between the first and second fixation portions, wherein the first fixation portion attaches to the first bridge element at any of a plurality of attachment locations, and wherein the second fixation portion attaches to the second bridge element at any of a plurality of attachment locations.

35. The implant of claim 26, further comprising:
a third bridge element comprising a fifth bridge end having a fifth anchoring feature, a sixth bridge end having a sixth anchoring feature, and a third bridge body extending between the fifth and sixth bridge ends, the third bridge element sized and shaped for securing to a vertebra in a medial-lateral orientation; and
a second bias element;
wherein the second bias element attaches to the second bridge element and to the third bridge element to provide a stabilizing force between the second and third bridge elements when the bridge elements are properly secured to three respective vertebrae.

36. The implant of claim 35, wherein the second bias element is formed either of an elastically deformable material to provide a dynamic stabilizing force between the second and third bridge elements or of a rigid material to provide a rigid stabilizing force between the second and third bridge elements.

37. The implant of claim 26, further comprising:
a second bias element comprising a first fixation portion, a second fixation portion and a bias body extending between the first and second fixation portions, wherein the first fixation portion attaches to the first bridge element at any of a plurality of attachment locations, and wherein the second fixation portion attaches to the second bridge element at any of a plurality of attachment locations.

38. The implant of claim 37, wherein the first fixation portion of the first bias element attaches to the first bridge element at a first location and the second fixation portion of the first bias element attaches to the second bridge element at a second location medial-laterally offset from the first location;
wherein the first fixation portion of the second bias element attaches to the first bridge element at a third location and the second fixation portion of the second bias element attaches to the second bridge element at a fourth location medial-laterally offset from the third location such that the second bias element crosses over or under the first bias element.

39. A spinal stabilization implant for attachment to a portion of a spine, the implant comprising:
a first bridge element comprising a first bridge end having a first anchoring feature, a second bridge end having a second anchoring feature, and a first bridge body extending between the first and second bridge ends, the first bridge element sized and shaped for securing to a vertebra in a medial-lateral orientation;
a second bridge element comprising a third bridge end having a third anchoring feature, a fourth bridge end having a fourth anchoring feature, and a second bridge body extending between the third and fourth bridge ends, the second bridge element sized and shaped for securing to a vertebra in a medial-lateral orientation;
a plurality of anchoring members, wherein a first anchoring member interfaces with the first anchoring feature for securing the first bridge end to a first vertebra, a second anchoring member interfaces with the second anchoring feature for securing the second bridge end to the first vertebra, a third anchoring member interfaces with the third anchoring feature for securing the third bridge end to a second vertebra, and a fourth anchoring member interfaces with the fourth anchoring feature for securing the fourth bridge end to the second vertebra; and
an elastically deformable first bias element that attaches to the first bridge element and the second bridge element to provide a dynamic stabilizing force between the bridge elements when the bridge elements are properly secured to two respective vertebrae, the first bias element comprising a first fixation portion, a second fixation portion and a bias body extending between the first and second fixation portions;

wherein the first fixation portion attaches to the first bridge element at a location medially offset from the first and second anchoring features, wherein the second fixation portion attaches to the second bridge element at a location medially offset from the third and fourth anchoring features, and wherein each anchoring feature comprises an aperture and each anchoring member comprises a screw sized and shaped to be received in the aperture, wherein each screw is individually polyaxially positionable relative to the anchoring feature when the screw is received in the aperture.

40. The implant of claim 39, wherein the first and second fixation portions removably attach to the corresponding bridge element at any one of a plurality of non-discrete attachment locations.

41. The implant of claim 39, wherein the first and second fixation portions removably attach to the corresponding bridge element at any one of a plurality of discrete attachment locations.

42. The implant of claim 39, further comprising:
a plurality of attachment mechanisms, wherein each attachment mechanism comprises a attachment portion for interfacing with a bias element to attach the bias element to one of the bridge elements.

43. The implant of claim 42, wherein the first and second fixation portions are attachable at any one of a plurality of discrete attachment locations with one of the attachment mechanisms, wherein the attachment mechanism further comprises a screw, wherein each bridge element comprises at least one hole extending through the bridge element, the hole sized and shaped to receive the screw; and
wherein the attachment mechanism is positionable such that tightening the screw locks the position of the attachment mechanism relative to the bridge element.

44. The implant of claim 42, further comprising:
a third bridge element, comprising a fifth bridge end having a fifth anchoring feature, a sixth bridge end having a sixth anchoring feature, and a third bridge body extending between the fifth and sixth bridge ends, the third bridge element sized and shaped for securing to a vertebra in a medial-lateral orientation, the third bridge element between the first and second bridge elements;
wherein the first bias element further comprises a middle portion between the first fixation portion and the second fixation portion, wherein the middle portion interfaces with an attachment mechanism to attach the middle portion to the third bridge element.

45. The implant of claim 39, wherein the first bias element comprises an elastically deformable member formed from material chosen from the group consisting of elastomers, silicones, urethanes, bio-absorbable materials, woven textile structures, knit textile structures, braided textile structures, molded thermoplastic polymers, ethylene-vinyl acetate, PEEK, UHMWPE, nitinol, titanium, and stainless steel, wherein the first bias element provides a dynamic stabilizing force between the bridge elements.

46. The implant of claim 45, wherein the first and second fixation portions are formed of a rigid material, wherein the bias body consists of the elastically deformable material.

47. The implant of claim 39, wherein the first bias element is removably attachable to the bridge elements such that the first bias element extends substantially perpendicular to the bridge elements.

48. The implant of claim 39, further comprising:
a third bridge element comprising a fifth bridge end having a fifth anchoring feature, a sixth bridge end having a sixth anchoring feature, and a third bridge body extending between the fifth and sixth bridge ends, the third bridge element sized and shaped for securing to a vertebra in a medial-lateral orientation; and
a second bias element;
wherein the second bias element attaches to the second bridge element and to the third bridge element to provide a stabilizing force between the second and third bridge elements when the bridge elements are properly secured to three respective vertebrae.

49. The implant of claim 48, wherein the second bias element is formed either of an elastically deformable material to provide a dynamic stabilizing force between the second and third bridge elements or of a rigid material to provide a rigid stabilizing force between the second and third bridge elements.

50. The implant of claim 39, further comprising:
a second bias element comprising a first fixation portion, a second fixation portion end and a bias body extending between the first and second fixation portions, wherein the first fixation portion attaches to the first bridge element at any of a plurality of attachment locations, and wherein the second fixation portion attaches to the second bridge element at any of a plurality of attachment locations.

51. The implant of claim 50, wherein the first fixation portion of the first bias element attaches to the first bridge element at a first location and the second fixation portion of the first bias element attaches to the second bridge element at a second location medial-laterally offset from the first location;
wherein the first fixation portion of the second bias element attaches to the first bridge element at a third location and the second fixation portion of the second bias element attaches to the second bridge element at a fourth location medial-laterally offset from the third location such that the second bias element crosses over or under the first bias element.

52. A spinal stabilization implant for attachment to a portion of a spine, the implant comprising:
a first bridge element comprising a first bridge end having a first anchoring feature, a second bridge end having a second anchoring feature, and a first bridge body extending between the first and second bridge ends, the first bridge element sized and shaped for securing to a vertebra in a medial-lateral orientation;
a second bridge element comprising a third bridge end having a third anchoring feature, a fourth bridge end having a fourth anchoring feature, and a second bridge body extending between the third and fourth bridge ends, the second bridge element sized and shaped for securing to a vertebra in a medial-lateral orientation;
a plurality of anchoring members, wherein a first anchoring member interfaces with the first anchoring feature for securing the first bridge end to a first vertebra, a second anchoring member interfaces with the second anchoring feature for securing the second bridge end to the first vertebra, a third anchoring member interfaces with the third anchoring feature for securing the third bridge end to a second vertebra, and a fourth anchoring member interfaces with the fourth anchoring feature for securing the fourth bridge end to the second vertebra;
a first bias element that attaches to the first bridge element and the second bridge element to provide a stabilizing force between the bridge elements when the bridge elements are properly secured to two respective vertebrae, wherein the first bias element comprises a cephalad fixation portion removably attachable to the first bridge element, a caudal fixation portion removably attachable to the second bridge element, and a bias body extending between the cephalad and caudal fixation portions, wherein the cephalad and caudal fixation portions attach to the corresponding bridge element at any one of a plurality of discrete attachment locations; and a plurality of attachment mechanisms, wherein each attachment mechanism comprises a attachment portion for interfacing with a bias element to attach the bias element to one of the bridge elements, wherein the cephalad and caudal fixation portions each attach at any one of the plurality of discrete attachment locations with one of the attachment mechanisms, wherein the attachment mechanism further comprises a screw, wherein each bridge element comprises at least one hole extending through the bridge element, the hole sized and shaped to receive the screw, and wherein the attachment mechanism is positionable such that tightening the screw secures the bias element to the attachment mechanism and locks the position of the attachment mechanism relative to the bridge element.

53. The implant of claim 52, further comprising:
a third bridge element, comprising a fifth bridge end having a fifth anchoring feature, a sixth bridge end having a sixth anchoring feature, and a third bridge body extending between the fifth and sixth bridge ends, the third bridge element sized and shaped for securing to a vertebra in a medial-lateral orientation, the third bridge element between the first and second bridge elements,
wherein the first bias element further comprises a middle portion between the cephalad end and the caudal end, wherein the middle portion interfaces with one of the attachment mechanisms to attach the middle portion to the third bridge element.

54. The implant of claim 52, wherein the first bias element comprises an elastically deformable member formed from material chosen from the group consisting of elastomers, silicones, urethanes, bio-absorbable materials, woven textile structures, knit textile structures, braided textile structures, molded thermoplastic polymers, ethylene-vinyl acetate, PEEK, UHMWPE, nitinol, titanium and stainless steel, wherein the first bias element provides a dynamic stabilizing force between the bridge elements.

55. The implant of claim 54, wherein the cephalad and caudal fixation portions are formed of a rigid material, and wherein the bias body consists of the elastically deformable material.

56. The implant of claim 52, wherein the first bias element is formed of a rigid material selected from the group consisting of titanium, stainless steel, aluminum, cobalt chromium, Nitinol, PEEK, and UHMWPE, wherein the first bias element provides a rigid stabilizing force between the bridge elements.

57. The implant of claim 52, wherein the first bias element removably attaches to the bridge elements such that the first bias element extends substantially perpendicular to the bridge elements.

58. The implant of claim 52, wherein the cephalad fixation portion of the first bias element attaches to the first bridge element and the caudal end of the first bias element attaches to the second bridge element such that the first bias element is substantially parallel to the sagittal plane.

59. The implant of claim 52, further comprising:
a second bias element comprising a cephalad fixation portion, a caudal fixation portion and a bias body extending between the cephalad and caudal fixation portions, wherein the cephalad fixation portion attaches to the first bridge element at any of a plurality of attachment locations, and wherein the caudal fixation portion attaches to the second bridge element at any of a plurality of attachment locations.

60. The implant of claim 52, further comprising:
a third bridge element comprising a fifth bridge end having an fifth anchoring feature, a sixth bridge end having a sixth anchoring feature, and a third bridge body extending between the fifth and sixth bridge ends, the third bridge element sized and shaped for securing to a vertebra in a medial-lateral orientation; and
a second bias element;
wherein the second bias element attaches to the second bridge element and to the third bridge element to provide a stabilizing force between the second and third bridge elements when the bridge elements are properly secured to three respective vertebrae.

61. The implant of claim 60, wherein the first bias element comprises an elastically deformable material to provide an dynamic stabilizing force between the first and second bridge elements, and wherein the second bias element is formed of a rigid material to provide a rigid stabilizing force between the second and third bridge elements.

62. A spinal stabilization implant for attachment to a portion of a spine, the implant comprising:
a first bridge element comprising a first bridge end having a first anchoring feature, a second bridge end having a second anchoring feature, and a first bridge body extending between the first and second bridge ends, the first bridge element sized and shaped for securing to a vertebra in a medial-lateral orientation;
a second bridge element comprising a third bridge end having a third anchoring feature, a fourth bridge end having a fourth anchoring feature, and a second bridge body extending between the third and fourth bridge ends, the second bridge element sized and shaped for securing to a vertebra in a medial-lateral orientation;
a plurality of anchoring members, wherein a first anchoring member interfaces with the first anchoring feature for securing the first bridge end to a first vertebra, a second anchoring member interfaces with the second anchoring feature for securing the second bridge end to the first vertebra, a third anchoring member interfaces with the third anchoring feature for securing the third bridge end to a second vertebra, and a fourth anchoring member interfaces with the fourth anchoring feature for securing the fourth bridge end to the second vertebra;
a first bias element that attaches to the first bridge element and the second bridge element to provide a stabilizing force between the bridge elements when the bridge elements are properly secured to two respective vertebrae, wherein the first bias element comprises a cephalad fixation portion removably attachable to the first bridge element, a caudal fixation portion removably attachable to the second bridge element, and a bias body extending between the cephalad and caudal fixation portions, wherein the cephalad and caudal fixation portions attach to the corresponding bridge element at any one of a plurality of discrete attachment locations; and
a second bias element comprising a cephalad fixation portion, a caudal fixation portion and a bias body extending between the cephalad and caudal fixation portions, wherein the cephalad fixation portion attaches to the first bridge element at any of a plurality of attachment locations, and wherein the caudal fixation portion attaches to the second bridge element at any of a plurality of attachment locations, wherein the cephalad fixation portion of the first bias element attaches to the first bridge element at a first location and the caudal fixation portion of the first bias element attaches to the second bridge element at a second location medial-laterally offset from the first location, and wherein the cephalad fixation portion of the second bias element attaches to the first bridge element at a third location and the caudal fixation portion of the second bias element attaches to the second bridge element at a fourth location medial-laterally offset from the third location such that the second bias element crosses over or under the first bias element.

63. The implant of claim 62, wherein the first bias element comprises an elastically deformable member formed from material chosen from the group consisting of elastomers, silicones, urethanes, bio-absorbable materials, woven textile structures, knit textile structures, braided textile structures, molded thermoplastic polymers, ethylene-vinyl acetate, PEEK, UHMWPE, nitinol, titanium and stainless steel, wherein the first bias element provides a dynamic stabilizing force between the bridge elements.

64. The implant of claim 63, wherein the cephalad and caudal fixation portions are formed of a rigid material, and wherein the bias body consists of the elastically deformable material.

65. The implant of claim 62, wherein the first bias element is formed of a rigid material selected from the group consisting of titanium, stainless steel, aluminum, cobalt chromium, Nitinol, PEEK, and UHMWPE, wherein the first bias element provides a rigid stabilizing force between the bridge elements.

66. The implant of claim 62, further comprising:

a third bridge element comprising a fifth bridge end having an fifth anchoring feature, a sixth bridge end having a sixth anchoring feature, and a third bridge body extending between the fifth and sixth bridge ends, the third bridge element sized and shaped for securing to a vertebra in a medial-lateral orientation; and wherein the second bias element attaches to the second bridge element and to the third bridge element to provide a stabilizing force between the second and third bridge elements when the bridge elements are properly secured to three respective vertebrae.

67. The implant of claim 66, wherein the first bias element comprises an elastically deformable material to provide an dynamic stabilizing force between the first and second bridge elements, and wherein the second bias element comprises a rigid material to provide a rigid stabilizing force between the second and third bridge elements.

* * * * *